(12) United States Patent
Acedo et al.

(10) Patent No.: US 11,933,775 B2
(45) Date of Patent: Mar. 19, 2024

(54) METHODS AND SYSTEMS FOR EVALUATING ECOLOGICAL DISTURBANCE OF AN AGRICULTURAL MICROBIOME BASED UPON NETWORK PROPERTIES OF ORGANISM COMMUNITIES

(71) Applicant: Biome Makers Inc., West Sacramento, CA (US)

(72) Inventors: Alberto Acedo, León (ES); Rüdiger Ortiz Álvarez, Madrid (ES); Ignacio Belda Aguilar, Madrid (ES); Nabeel Imam, Santiago (CL); Daniel Almonacid, Lafayette, CA (US); Adrian Ferrero, La Bañeza (ES)

(73) Assignee: Biome Makers Inc., Davis, CA (US)

(*) Notice: Subject to any disclaimer, the term of this patent is extended or adjusted under 35 U.S.C. 154(b) by 393 days.

(21) Appl. No.: 17/119,972

(22) Filed: Dec. 11, 2020

(65) Prior Publication Data
US 2021/0181176 A1    Jun. 17, 2021

Related U.S. Application Data

(60) Provisional application No. 62/947,493, filed on Dec. 12, 2019.

(51) Int. Cl.
*G01N 33/24* (2006.01)
*A01B 79/00* (2006.01)

(52) U.S. Cl.
CPC .......... *G01N 33/24* (2013.01); *A01B 79/005* (2013.01); *G01N 2033/245* (2013.01)

(58) Field of Classification Search
CPC . G01N 33/24; G01N 2033/245; A01B 79/005
(Continued)

(56) References Cited

U.S. PATENT DOCUMENTS

2011/0137456 A1    6/2011   Koselka et al.
2016/0121325 A1*   5/2016   Masquelier ......... B01L 3/50273
                                                422/561
(Continued)

FOREIGN PATENT DOCUMENTS

WO    WO-2021119528 A1 *   6/2021   ........... A01B 79/005

OTHER PUBLICATIONS

Wu, "ezTree: an automated pipeline for identifying phylogenetic marker genes and inferring evolutionary relationships among uncultivated prokaryotic draft genomes", 2017. (Year: 2017).*

(Continued)

*Primary Examiner* — Michael P Nghiem

(57) ABSTRACT

Inventions include methods and systems for evaluation of agriculture sites and execution of actions for improving various site parameters in a sustainable manner. In embodiments, a method for characterization and improvement of an agricultural site includes: receiving a set of agriculture samples from an agriculture site or in association with an agricultural process; generating sample data upon processing the set of samples with a set of sample processing operations; generating a set of features upon performing a set of transformation operations upon the set of data streams; returning an analysis characterizing a status of the agriculture site in relation to at least one perturbation, upon processing the set of features; and executing an action for at least one of maintaining and improving the agriculture site, based upon the analysis. The inventions implement features associated with composition, network properties, and emergent properties as biomarkers for characterizing statuses of sites under analysis.

22 Claims, 11 Drawing Sheets

(58) Field of Classification Search
USPC .......................................................... 702/2
See application file for complete search history.

(56) References Cited

U.S. PATENT DOCUMENTS

| | | | |
|---|---|---|---|
| 2017/0223947 A1* | 8/2017 | Gall ..................... | A01B 79/005 |
| 2018/0363031 A1 | 12/2018 | Becares et al. | |
| 2021/0010993 A1* | 1/2021 | Shibata ................ | A01B 79/005 |
| 2021/0051956 A1* | 2/2021 | Qian ..................... | A01N 43/16 |
| 2022/0240432 A1* | 8/2022 | Acedo .................. | A01C 21/002 |
| 2022/0246241 A1* | 8/2022 | Acedo .................. | A01C 21/002 |

OTHER PUBLICATIONS

Schmidt et al. "Agricultural management and plant selection interactively affect rhizosphere microbial community structure and nitrogen cycling", Microbiome vol. 7, Article No. 146, Jul. 11, 2019. Retrieved on Jul. 2, 2021. USA.

Girvan et al. "Community structure in social and biological networks", PNAS vol. 99, issue 12, Jun. 11, 2002. USA.

Van Klompenburg et al. "Crop yield prediction using machine learning: A systematic literature review", Computers and Electronics in Agriculture. 177(2020)105709, Aug. 18, 2020.

Konopka, Allan. "What is microbial community ecology", The ISME Journal. (2009) 3, 1223-1230. Aug. 6, 2009.

Netz et al. "Estimating computational limits on theoretical descriptions of biological cells", PNAS vol. 118, issue 6, Jan. 25, 2021. USA.

Veech, Joseph A. "A probablistic model for analysing species co-occurrence", Global Ecology and Biogeography, 2012.

Watts, et al. "Collective dynamics of 'small-world' networks". Nature vol. 393. Jun. 4, 1998.

Zele et al. "Ecology and evolution of facilitation among symbionts". Nature Communications (2018)9:4869.

* cited by examiner

METHODS AND SYSTEMS FOR EVALUATING ECOLOGICAL DISTURBANCE OF AN AGRICULTURAL MICROBIOME BASED UPON NETWORK PROPERTIES OF ORGANISM COMMUNITIES

CROSS-REFERENCE TO RELATED APPLICATIONS

This application claims the benefit of U.S. Provisional Application No. 62/947,493 filed on 12 Dec. 2019, which is incorporated in its entirety herein by this reference.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A READ-ONLY OPTICAL DISC, AS A TEXT FILE OR AN XML FILE VIA THE PATENT ELECTRONIC SYSTEM

Not Applicable

STATEMENT REGARDING PRIOR DISCLOSURES BY THE INVENTOR OR A JOINT INVENTOR

Not Applicable

FIELD OF THE INVENTION

The disclosure generally relates to tools and systems implementing methods for evaluating effects of products and practices on agricultural ecosystems.

BACKGROUND

Agriculture ecosystems are human-managed ecosystems subject to various ecological rules, in relation to steady state scenarios and in response to various perturbations. Understanding the ecological mechanisms behind soil microbial communities is a fruitful way to improve management practices, test various products, evaluate sustainability, and therefore improve plant productivity. Acquisition and processing of the appropriate data from agriculture-associated samples, development of models for characterization of ecosystem statuses, and generation of outputs and implementation of actions for maintaining such ecosystems and/or improving yields in a sustainable manner are all areas of innovation in which the inventions described herein provide value.

BRIEF SUMMARY OF THE INVENTION

The disclosure provides embodiments, variations, and examples of a method for characterization and improvement of an agricultural site, the method comprising: receiving a set of agriculture samples from an agriculture site, in association with a perturbation to the agriculture site; generating a sample dataset upon processing the set of samples with a set of sample processing operations that characterize the microbial composition of said set of samples; generating a set of features upon performing a set of transformation operations upon the sample dataset, wherein the set of features are associated with a set of network properties of organisms of the set of samples; returning an analysis characterizing a status of the agriculture site in relation to the perturbation, upon processing the set of features; and executing an action for at least one of maintaining and improving the status of the agriculture site, based upon the analysis. Additional aspects of the invention(s) are provided below.

DETAILED DESCRIPTION OF THE INVENTION(S)

Figure 1:
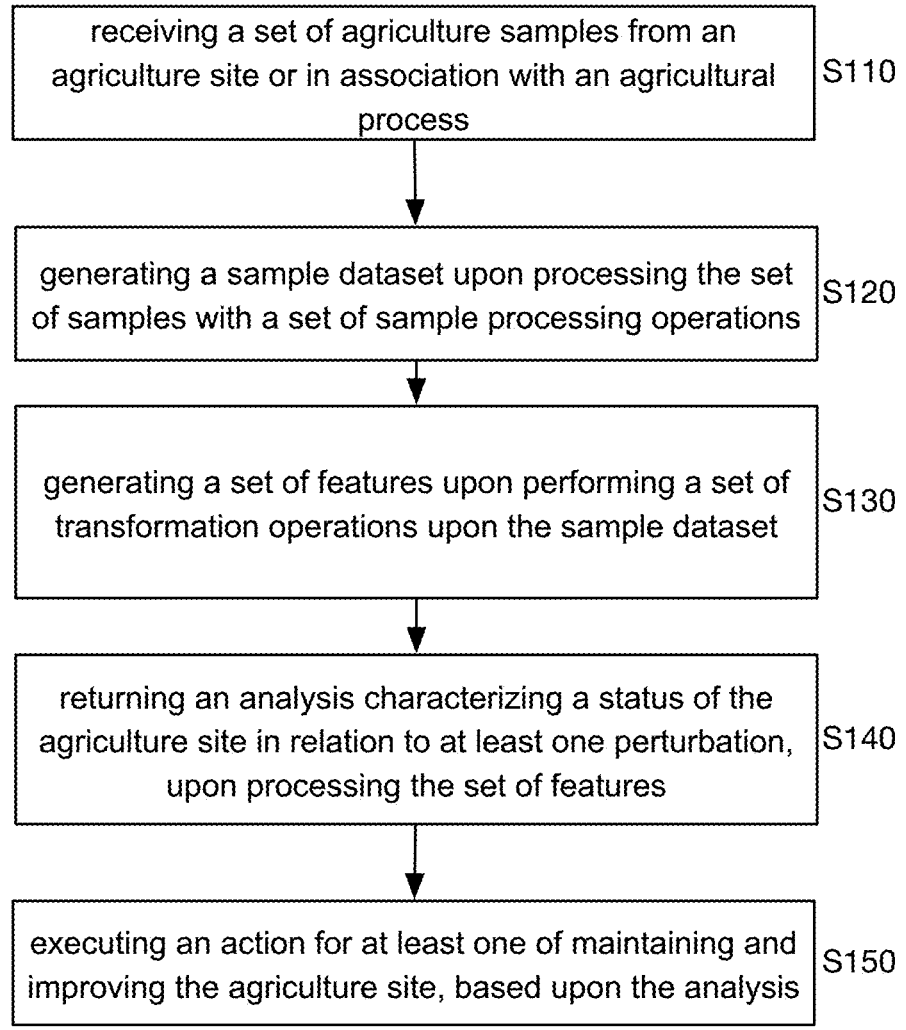
FIG. 1 depicts an embodiment of a workflow of a method for agriculture site analysis.

The following description of the preferred embodiments of the invention is not intended to limit the invention to these preferred embodiments, but rather to enable any person skilled in the art to make and use this invention.

1. Benefits

The invention(s) described can confer several benefits over conventional systems, methods, and compositions.

The invention(s) provide systems and methods for assessing soil health beyond traditional biodiversity descriptors, with respect to developing models for analysing community-level properties, and implementation of actions for improving or maintaining health of an agricultural ecosystem and improving productivity in a sustainable manner.

In embodiments, the invention(s) provide methods for determining ecological emergent properties through the inference of network properties in local microbial, fungal, and/or other organism communities, and to use them to assess the impact of different management practices (e.g., farming practices) on soil ecosystem functioning (e.g., for farms, for vineyards, for other agricultural ecosystems, etc.). In examples, assessment of fungal communities according to the invention(s) described produced characterization of small-world network arrangements to more random arrangements with differential levels of niche specialization, in relation to geographic factors, climatic factors, and management practices. In more detail, according to the example, local network properties were associated with assembly patterns and variations derived from land management practices. Low-intervention practices (e.g., organic and biodynamic managements) promoted densely clustered networks, describing an equilibrium state based on mixed-collaborative communities. On the contrary, conventionally managed land had highly modular sparser communities, supported by a higher co-exclusion proportion. As such, the model was trained to process network properties and to return predicted management practices, environmental factors, and ecosystem disturbances.

In embodiments, the method(s) promote agro-ecosystem sustainability through assessment of soil organism communities. In particular, the complexity of microbial communities, at both taxonomic and functional levels, is impossible to assess practically without systems and methods described herein, where the methods cannot be practically implemented in the human mind. The invention(s) thus process samples to extract patterns connecting sample microbiome composition with ecosystem function in order to drive interventions based upon the impact of biotic (e.g., interspecies interactions, intraspecies interactions) and abiotic (e.g. climate or anthropogenic disturbances) factors. As such, the invention(s) provide a new methodological framework-inferring emergent properties from local networks—with assessment and guidance of different ecological strategies in agricultural site communities.

Additionally, the inventions described provide systems and a platform including architecture for agriculture sample extraction and processing, which provide improved tools for monitoring, forecasting, and responding to events (e.g., changes in productivity, events associated with management practices, environmental perturbations, product-induced perturbations, etc.) associated with one or more agricultural sites. Additionally or alternatively, the inventions can assess implementation of a plant variety and/or a seed variety at an agriculture site.

Additionally, the inventions described implement rapid processing of samples and data generated from sample processing, in order to extract insights related to effects of management practices and/or products on various agricultural sites, in a manner that cannot be practically performed in the human mind.

Additionally, the inventions apply outputs of the analyses to effect one or more actions (e.g., treatments) to maintain or improve site conditions, thereby providing practical applications of the method(s) and models involved.

Additionally, the inventions involve collection of samples from various agricultural sites, processing of samples to extract data features, application of one or more transformations to the data features to generate modified digital objects, create improved training data sets for machine learning/classification algorithms, and iteratively train the machine learning/classification algorithms, such that agriculture site statuses can be returned upon processing subsequent samples.

Additionally or alternatively, the invention(s) can confer any other suitable benefit.

1.1 Definitions

The terms microbiome, microbiome information, microbiome data, microbiome population, microbiome panel and similar terms are used in the broadest possible sense, unless expressly stated otherwise, and would include: a census of currently present microorganisms, both living and non-living, which may have been present months, years, millennia or longer; a census of components of the microbiome other than bacteria and archaea (e.g., viruses, microbial eukaryotes, etc.); population studies and characterizations of microorganisms, genetic material, and biologic material; a census of any detectable biological material; and information that is derived or ascertained from genetic material, biomolecular makeup, fragments of genetic material, DNA, RNA, protein, carbohydrate, metabolite profile, fragment of biological materials and combinations and variations of these.

As used herein, the terms real-time microbiome data or information includes microbiome information that is collected or obtained at a particular setting or stage of an agricultural process for one or more agricultural sites.

As used herein, the terms derived microbiome information and derived microbiome data are to be given their broadest possible meaning, unless specified otherwise, and includes any real-time, microbiome information that has been computationally linked or used to create a relationship.

As used herein, the terms predictive microbiome information and predictive microbiome data are to be given their broadest possible meaning, unless specified otherwise, and includes information that is based upon combinations and computational links or processing of historic, predictive, real-time, and derived microbiome information, data, and combinations, variations and derivatives of these, which information predicts, forecasts, directs, or anticipates a future occurrence, event, state, or condition in the industrial setting, or allows interpretation of a current or past occurrence.

Real time, derived, and predicted data can be collected and stored, and thus, become historic data for ongoing or future decision-making for a process, setting, or application.

"Nucleic acid," "oligonucleotide," and "polynucleotide" refer to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. The term nucleic acid is used interchangeably with gene, cDNA, and mRNA encoded by a gene.

The term "microbiome", as used herein, refers to the ecological community of commensal, symbiotic, or pathogenic microorganisms in a sample.

The term "genome" as used herein, refers to the entirety of an organism's hereditary information that is encoded in its primary DNA sequence. The genome includes both the genes and the non-coding sequences. For example, the genome may represent a microbial genome or a mammalian genome.

Reference to "DNA region" should be understood as a reference to a specific section of genomic DNA. These DNA regions are specified either by reference to a gene name or a set of chromosomal coordinates. Both the gene names and the chromosomal coordinates would be well known to, and understood by, the person of skill in the art. In general, a gene can be routinely identified by reference to its name, via which both its sequences and chromosomal location can be routinely obtained, or by reference to its chromosomal coordinates, via which both the gene name and its sequence can also be routinely obtained.

Reference to each of the genes/DNA regions detailed above should be understood as a reference to all forms of these molecules and to fragments or variants thereof. As would be appreciated by the person of skill in the art, some genes are known to exhibit allelic variation or single nucleotide polymorphisms. SNPs encompass insertions and deletions of varying size and simple sequence repeats, such as dinucleotide and trinucleotide repeats. Variants include nucleic acid sequences from the same region sharing at least 90%, 95%, 98%, 99% sequence identity i.e. having one or more deletions, additions, substitutions, inverted sequences etc. relative to the DNA regions described herein. Accordingly, the present invention should be understood to extend to such variants which, in terms of the present applications, achieve the same outcome despite the fact that minor genetic variations between the actual nucleic acid sequences may exist between different bacterial strains. The present invention should therefore be understood to extend to all forms of DNA which arise from any other mutation, polymorphic or allelic variation.

The term "sequencing" as used herein refers to sequencing methods for determining the order of the nucleotide bases-adenine, guanine, cytosine, and thymine—in a nucleic acid molecule (e.g., a DNA or RNA nucleic acid molecule.

The term "barcode" as used herein, refers to any unique, non-naturally occurring, nucleic acid sequence that may be used to identify the originating genome of a nucleic acid fragment.

A "computer-readable medium", is an information storage medium that can be accessed by a computer using a commercially available or custom-made interface. Exemplary computer-readable media include memory (e.g., RAM, ROM, flash memory, etc.), optical storage media (e.g., CD-ROM), magnetic storage media (e.g., computer hard drives, floppy disks, etc.), punch cards, or other commercially available media. Information may be transferred between a system of interest and a medium, between computers, or between computers and the computer-readable medium for storage or access of stored information. Such transmission can be electrical, or by other available methods, such as IR links, wireless connections, etc.

2. Methods

As shown in FIG. 1, an embodiment of a method 100 for characterization and improvement of an agricultural site includes: receiving a set of agriculture samples from an agriculture site or in association with an agricultural process S110; generating a sample dataset upon processing the set of samples with a set of sample processing operations S120; generating a set of features upon performing a set of transformation operations upon the sample dataset S130; returning an analysis characterizing a status of the agriculture site in relation to at least one perturbation, upon processing the set of features S140; and executing an action for at least one of maintaining and improving the agriculture site, based upon the analysis S150.

The method 100 functions to characterize statuses of agricultural sites (e.g., in response to environmental perturbations, in response to implementation of a plant variety and/or a seed variety at an agriculture site, in response to management practices, in response to implementation of products, in relation to site productivity, in relation to disease states, in equilibrium, etc.) and to execute actions and interventions for maintaining and/or improving statuses of the agricultural site(s) in a sustainable manner. As such, the method(s) can provide steps for monitoring, controlling, and analysis of agriculture activities, with practical applications in food production, viticulture, bio-fuel production, and other agricultural activities.

Beyond characterizing ecological communities in terms of community aggregated traits (CATs), which result from the aggregation of taxa characteristics, the methods described provide characterizations and guidance for interventions based upon emergent properties (EPs) arising from specific taxa combinations and/or other features. In particular, the invention(s) produce models with architecture for contextualization of emergent properties into ecological mechanisms, with functionality for returning predictions of how communities would behave under various circumstances. Additionally, translating the idiosyncratic community behaviours into a measurable metric enables microbiome monitoring applications, such as in sustainable farming, food production, or human health. The methods thus discover, identify, and implement new biomarkers of soil health and create tools to provide accessibility of such information and guidance to land managers.

The method(s) described can be implemented by systems and platforms described in Section 3 below. Additionally or alternatively, the method(s) described can be implemented by embodiments, variations, and examples of systems described in U.S. application Ser. No. 15/779,531 filed on 28 May 2018, which is herein incorporated in its entirety by this reference.

2.1 Methods—Sample Reception

Step S110 recites: receiving a set of agriculture samples from one or more agriculture sites or in association with an agricultural process, which functions to provide source material for generation of data from which models for characterizing statuses of the agriculture site(s) and/or various perturbations in downstream steps.

In step S110, samples can be received from various portions of the agriculture site(s) and/or states of processing of crops or other products derived from the agriculture site. In embodiments, samples can be extracted from soil, another substrate, water used in agriculture, from various portions of crops, from organisms interacting with crops (e.g., parasites, other symbiotic organisms, etc.), from consumable products (e.g., food, beverages, supplements, etc.) derived from crops, from other surfaces (e.g., conduits used to deliver water or nutrients to crops, etc.), and/or from other suitable sampling sites. The samples can include solid samples (e.g., soil, sediment, rock, food samples). The samples can additionally or alternatively include liquid samples (e.g., surface water, sub-surface water, other liquids derived from crops, consumable products derived from crops, crop-derived products at various stages of processing or fermentation, etc.). The samples can additionally or alternatively include gas samples (e.g., samples from gases obtained from a greenhouse, gases produced during processing of crops or crop-derived products, etc.).

In relation to step S110, sample reception can be performed using equipment (e.g., machinery, robotic apparatus configured to traverse an agricultural site in coordination with retrieval of the set of agriculture samples, other apparatus) and/or manually. In variations, sample reception performed in Step S110 can use any one or more of: an instrument (e.g., scoop for soil, sharp instrument for extracting a portion of a crop specimen, etc.), a permeable substrate (e.g., a swab, a sponge, etc.), a non-permeable substrate (e.g., tape, etc.), a container (e.g., vial, tube, bag, etc.) configured to receive a sample from the agriculture site or associated crops, and any other suitable sample-reception element. In a specific example, samples can be collected from one or more of: soil, other crop-associated solids, water, other crop-associated liquids, gases, and a crop component (e.g., root, stem, leaf, flower, seed, other plant component, etc.). In relation to soil samples, samples can be extracted in relation to a reference point (e.g., distance from surface, distance from plant, etc.). In relation to plant components, samples can be taken from a reference (e.g., distance from leaf, distance, from node, distance along root, etc.). In variations in which multiple samples are taken, samples can be pooled (e.g., combined) or kept distinct.

In relation to step S110, samples can be acquired once, or at several time points within a time period or in relation to a process (e.g., process associated with crop handling, fermentation process, process for preparing crops for consumption, etc.). The time period can be on the order of seconds, minutes, hours, days, months, years, decades, or of any other suitable time scale.

Furthermore, samples can be received from one or more metacommunities, where a metacommunity is defined as a group of communities within the same habitat/region/pool associated with each agriculture site associated with the set of samples, where the group(s) of communities display multiple possible arrangements according to environmental filters, dispersal restrictions, priority effects and the latter established interactions. As such, features, insights, and actions implemented in subsequent steps of the method can be generated or performed at the metacommunity level and/or at local levels of abstraction.

In one example, step S110 involved extraction of soil samples from vineyards from multiple geographic locations (e.g., U.S, Spain) over a certain time period (e.g., years). In the example, the samples were taken from topsoil, at a 30 cm distance from the vine trunk, within a depth between 5-10 cm.

In other examples, however, samples can be acquired in another suitable manner or from other suitable sources.

2.2 Methods—Sample Processing

Step S120 recites: generating a sample dataset upon processing the set of samples with a set of sample processing operations, which functions to process raw sample material with one or more operations, thereby generating base data from which features can be extracted in subsequent portions of the method. In step S120, processing the set of samples can include wet lab processing techniques (e.g., sample lysis, sample enrichment, sample purification, target material capture or separation, target amplification, etc.), as well as sequencing and library preparation operations. As such, generating sample data in step S120 includes a combination of sample processing techniques (e.g., wet laboratory techniques) and computational techniques (e.g., utilizing tools of bioinformatics) to quantitatively and/or qualitatively characterize the microbiome, functional features, and/or other aspects (e.g., chemistry) of each sample of the agriculture site(s). Sample processing operations can include generation of one or more of: a full metagenomic dataset, a metatranscriptomics dataset, and a proteomics dataset.

As such, in variations, step S120 can include one or more of: sample storage (e.g., at appropriate conditions prior to subsequent processing); sample lysis (e.g., using physical methods, using chemical methods, using biological methods, etc.); genetic material (e.g., nucleic acid material) extraction including extraction of DNA, RNA, nucleic acid fragments, or other nucleic acid material; protein extraction; nucleic acid purification (e.g., using precipitation, using liquid-liquid based purification, using chromatography, using binding moiety functionalized particles, etc.); target material capture; removal of sample waste; target incubation; target amplification (e.g., using polymerase chain reaction (PCR)-based techniques, using helicase-dependent amplification (HDA), using loop mediated isothermal amplification (LAMP), using self-sustained sequence replication (3SR), using nucleic acid sequence based amplification (NASBA), using strand displacement amplification (SDA), using rolling circle amplification (RCA), ligase chain reaction (LCR), etc.); target enrichment; and/or any other suitable sample processing steps.

In relation to amplification of nucleic acids, primers used can be designed to mitigate amplification bias effects, as well as configured to amplify nucleic acid regions/sequences (e.g., of the 16S region, the ITS region, etc.) that are informative taxonomically, phylogenetically, in relation to emergent properties, for formulations, and/or for any other suitable purpose. Primers used in variations of Block S120 can additionally or alternatively include incorporated barcode sequences, unique molecule identifiers, adaptor sequences, or other sequences specific to each sample and/or in association with sequencing platforms, which can facilitate identification of material derived from individual samples post-amplification. Examples of custom primers are described in WO 2017/096385 published 8 Jun. 2017, which is herein incorporated in its entirety by this reference.

Furthermore, sequencing can be performed in coordination with a next generation sequencing platform (e.g., Illumina™ sequencing platform) or other suitable sequencing platform (e.g., nanopore sequencing platform, PacBio platform, MinION platform, etc.). Additionally or alternatively, any other suitable sequencing platform or method can be used (e.g., a Roche 454 Life Sciences platform, a Life Technologies SOLiD platform, etc.). Additionally or alternatively, sample processing can implement any other step configured to facilitate processing (e.g., using a Nextera kit) for performance of a fragmentation operation (e.g., fragmentation and tagging with sequencing adaptors) in cooperation with amplification. Additionally or alternatively, filtering of sequences (e.g., chimeric sequences, other sequences, etc.) can be performed in coordination with step S120.

In examples of sample processing according to step S120, soil samples were stored at −80° C. until DNA extraction, where DNA extraction was performed using a kit for extraction of organism DNA (e.g., DNeasy PowerLyzer PowerSoil Kit™, Qiagen™). Libraries were then prepared following a two-step PCR protocol (e.g., associated with an Illumina™ platform and protocol), and sequenced on an Illumina MiSeq™ platform using paired end sequencing (e.g., at 2×300 bp). Libraries were generated upon amplification and sequencing of target regions (e.g., 16s rRNA V4 region, the ITS1 region, etc.) using custom primers as described above, and raw sequences were analyzed using VSEARCH using default parameters. Briefly, raw paired-end FASTQ sequences were merged, filtered by an expected error 0.25, dereplicated, and sorted by size. Chimera sequences were filtered out, and remaining sequences were clustered non-singleton sequences into 97% identity operational taxonomic units (OTUs). All combined sequences were then mapped to a list of 31,516 OTUs with at least 97% identity, resulting in an OTU table with 54,738,544 sequences, averaging 156,395 sequences per soil sample. Samples had only a fraction of OTU richness, averaging 529 OTUs (e.g., in relation to a range of 23-4999 OTUs) per soil sample. OTUs were then classified (e.g., with a UNITE database according to a UTAX pipeline, with a SILVA 123 database through a SILVA-NGS pipeline). However, variations of the example can implement other sequencing protocols, OUT mapping, OUT classification algorithms, and/or other methods.

In variations, the method can additionally or alternatively include processing and assessment of amplicon sequence variants (ASVs). In particular, Dduring sequencing, it is expected that some nucleotides may be wrong because of sequencing errors; thus, the reads are clustered together to compensate for this, grouping similar sequences to form clusters which are represented by the centroid sequence (i.e., the most abundant sequence of the cluster). In situations where a 97% sequence identity threshold for OTUs is too inclusive for some families of species, processes of the method can include clusterization between sequences with a difference of only one nucleotide, in order to maintain the highest possible granularity and keep small differences visible, such that they can be annotated separately. Thus, in certain variations, ASV-associated approaches can significantly increase the number of final sequences to annotate for the same sample, increasing resolution and allowing better discrimination of closely related species. This approach can also allow performing of annotation of ASVs against curated taxonomic databases based on exact sequence matches which allows assessing in silico performance metrics for the annotation of each ASV. In specific applications, 16S ASVs provided suitable performance metrics (e.g., >90% sensitivity, >90% specificity, >90% positive predictive value, >90% negative predictive value) for identifying ~46% of the species and ~89% of the genera. ITS ASVs also provided good performance metrics for identifying ~87% of species and ~97% of the genera.

In variations, Bayes factors derived from the posterior odds of a connection between OTUs or ASVs can be used as edge-weights for weighted directed networks, and derivative features processed by models associated with the methods.

In relation to sample acquisition and sequencing, sample data can be tagged with contextual data, in order to couple identified sample features with various conditions (e.g., perturbations, products, environmental conditions, etc.) in downstream steps of the method. In variations, contextual data can include one or more of: geographic location (e.g., latitude, longitude, altitude); meteorological metadata (e.g., from Dark Sky API); climatic information (e.g., precipitation intensity, precipitation probability, maximum temperature, minimum temperature, dew point, humidity, environmental pressure, wind speed, wind bearing, wind gust, cloud cover, UV index, etc.); environmental disaster information (e.g., fires, hurricanes, tornadoes, earthquakes, temperature variations, etc.); organic management practices (e.g., integrating cultural, biological, and mechanical practices that foster cycling of resources, promote ecological balance, and conserve biodiversity without use of synthetic fertilizers, sewage, irradiation, and genetic engineering); non-organic management practices; use of synthetic fertilizers; use of natural fertilizers; biodynamic management practices (e.g., with generation of their own fertility through composting, integrating animals, cover cropping, and crop rotation); conventional management practices (e.g., with standard farming systems, using a variety of synthetic chemical fertilizers, pesticides, herbicides and other continual inputs, etc.).

In variations, perturbations can include one or more of: a management practice (e.g., a conventional management practice, an organic management practice, and a biodynamic management practice); a regenerative practice (e.g., application of one or more of a cover crop, silvopasture, managed grazing, and intercropping, etc.); a biological input including one or more of: a biostimulant, a biofertilizer, a biocontrol agent, a biopesticide, compost, and a biodynamic preparation (wherein the biological input is applied by one or more of: a broadcast spray, an in-furrow spray, seed treatment, application to soil with incorporation, and application to soil without incorporation, etc.); a natural ecological disturbance; and another suitable perturbation.

Data can additionally or alternatively be tagged with metacommunity descriptors, where a metacommunity is defined as a group of communities within the same habitat/region/pool associated with each agriculture site associated with the set of samples, where the group(s) of communities display multiple possible arrangements according to environmental filters, dispersal restrictions, priority effects and the latter established interactions. As such, in subsequent steps of the method 100, computing architecture for merging the metacommunity-inferred associations into each of the local communities associated with the set of samples, enables returning of estimations of network properties in all the local communities within the metacommunity, individually, obtaining sample(site)-specific information on microbial ecosystem functioning. Such processes also enable direct comparison among network properties of individual samples, even in the absence of common taxa among them, as all samples are mapped back to the metacommunity, thereby providing a normalization step. Thus, these emergent properties can be implemented as machine-determined universal biomarkers of ecological disturbance.

In relation to model architecture associated with training and refinement of machining learning models described further below, the method described in relation to step S120 can be used to create training sets of data, in coordination with step S130 below. As such, training data covering specific sample features and corresponding contextual information related to management practices and other perturbations (e.g., use of various products, environmental perturbations, etc.) can be used refine models for predicting effects of various practices and perturbations, and to guide future management practices in a sustainable manner.

In order to process such data, computing platforms implementing one or more portions of the method can be implemented in one or more computing systems, wherein the computing system(s) can be implemented at least in part in the cloud and/or as a machine (e.g., computing machine, server, mobile computing device, etc.) configured to receive a computer-readable medium storing computer-readable instructions. However, step S120 can be performed using any other suitable system(s).

2.3 Methods—Data Transformation for Extraction of Features including Emergent Properties Step S130 recites: generating a set of features upon performing a set of transformation operations upon the sample dataset, which functions to extract features associated with network properties of sequences associated with organisms. Step S130 can additionally or alternatively generate microbiome composition/community features (e.g., in relation to taxonomical features), as described above. As such, step S130 can be used to generate features that can be processed by models generated and trained as described below, in order to better understand the ecological processes and mechanisms behind community assembly. In subsequent steps, such network properties and their relationships can be contextualized as emergent properties, which can be used to characterize statuses and responses to perturbations with respect to the agriculture site(s) being assessed.

In more detail, step S130 functions to generate features that go beyond Community Aggregated Traits (CATs) associated with constituent taxa of the set of samples, by generating features based upon emergent properties that arise from specific community arrangements. Such emergent properties are then processed to generate insights related to the functionality of crop communities (e.g., seed survival rate), microbial communities (e.g., biofilm density, as a cause of composition behaviour), and/or other communities in subsequent steps.

In relation to step S130, the computing platform described can process outputs of step S120 to generate a community dataset characterizing communities of organisms associated with the sample(s) acquired in step S110. Generating the community dataset can include one or more of: rarefying samples to a desired sequencing depth in order to provide a desired level of detectability of OTUs of the sample(s); filtering OTUs with a desired threshold condition (e.g., retaining OTUs represented in a threshold number of samples); implementing a test for assessing that local communities are represented adequately (e.g., using a Mantel test of Bray Curtis dissimilarities); transforming one or more data outputs derived from step S120 to include presence and absence factors with respect to co-inclusion and/or co-exclusion of individual species (or other taxonomic units); retrieving significant co-inclusion and co-exclusion properties (e.g., for samples associated with individual sites, independently of each other), in order to provide data representing potential for interactions in complete metacommunity and/or environmental distributions (e.g., thereby generating a first grouping of positive pairs of organisms and a second grouping of negative pairs of organisms); and performing other suitable data transformation steps.

Then, to generate a network property dataset, the computing platform described can process the community dataset with architecture for implementing one or more processes including: transforming the first grouping of positive pairs of organisms and second grouping of negative pairs of organisms (related to co-inclusion and co-exclusion, respectively) into one or more aggregate matrices representing the possibility of co-inclusion (e.g., the whole number of potential associations between all the taxa in the pool, associations that are described as system relevant interdependencies including: biotic interactions, environmental affinities, dispersal restrictions, etc.) and co-exclusion of species (or other taxonomic units) in the metacommunity(ies) associated with the set of samples; subdividing the one or more aggregate matrices into a set of individual matrices containing features associated with only the species (or other taxonomic units) occurring in each of the set of samples; performing co-inclusions and/or co-exclusion estimations in another suitable manner (e.g., based upon covariance determination methods, based upon correlation determination methods, with SparCC, with SPIECeasi etc.); processing the set of individual matrices in order to generate a set of undirected network mappings with nodes representing species (or other taxonomic units) and edges representing statistically significant co-inclusions/co-exclusions; and performing other suitable data processing steps. Then, in relation to step S130, the computing platform can implement architecture for extracting features from the set of undirected network mappings, where features can include one or more of: a number of connected components (i.e., defined in relation to a subnetwork in which any two nodes connect to each other by edges, that lack connection to other nodes in the full network); a modularity factor (e.g., a quality of a partition into modules such as groups of nodes using a quantity of edges inside modules compared to a quantity of edges between modules, using an appropriate clustering algorithm (e.g. walktrap, Louvain, fast greedy, edge-betweenness, etc.); a clustering coefficient (e.g., based upon a transitivity determination and defined as a the ratio of triangles to connected triples in a respective network); an average path length between network components (i.e., defined as a mean of the minimal number of required edges to connect any two nodes); an assortativity factor (e.g., a feature which measures homophyly of a network, according to node properties or labels such as node degree, which quantifies the number of edges associated to a node); a proportion of co-inclusion factor normalized to a total number of combinations of all OTUs in the sample(s); a proportion of co-exclusion factor normalized to a total number of combinations of all OTUs in the sample(s); and other suitable features. In variations, networks can be visualized or rendered by the computing platform, in order to generate depictions of network topology in multidimensional space (e.g., in relation to generation of reports or execution of actions described in further detail below).

As described above, step S130 can also generate features associated with compositional aspects and/or functional aspects of the sample(s) from the agriculture site(s). For instance, compositional and functional aspects can include compositional aspects at the microorganism level, including parameters related to distribution of microorganisms across different groups of kingdoms, phyla, classes, orders, families, genera, species, subspecies, strains, infraspecies taxon (e.g., as measured in total abundance of each group, relative abundance of each group, total number of groups represented, etc.), and/or any other suitable taxa. Compositional and functional aspects can also be represented in terms of operational taxonomic units (OTUs) or other units. Compositional and functional aspects can additionally or alternatively include compositional aspects at the genetic level (e.g., regions determined by multi-locus sequence typing, 16S sequences, ITS sequences, other genetic markers, other phylogenetic markers, etc.). Compositional and functional aspects can include the presence or absence or the quantity of genes associated with specific functions (e.g., enzyme activities, disease resistance, organism-generated products, nutrient production, etc.).

Network properties can be determined for different types of organism communities (e.g., bacterial communities, fungal communities, etc.) independently of each other or in an aggregated manner.

Network properties can further include local network features extracted from a metacommunity network, and network properties for co-exclusion networks and network properties for co-inclusion networks.

2.3.1 Statistical Analyses

In variations, features can additionally or alternatively be processed with one or more statistical or other mathematical processes, in order to generate derivative features derived from outputs of steps S120 and/or S130. For instance, processing of features can include one or more of: implementation of principal component analysis (PCA) methods; generating measurements of variance; implementation of correlative tests (e.g., Spearman correlations); implementation of variance tests (e.g., Kruskal-Wallis tests); implementation of multidimensional scaling processes (e.g., a nonmetric multidimensional scaling (nMDS) algorithm); performing probabilistic methods; implementation of statistical models (e.g., generalized linear models, etc.); and performing other suitable statistical tests.

2.3.2 First Example of Generation of Network Properties

In a first example of generation of network properties informative of agriculture site characteristics, step S130 included: preparation of a microbial community dataset. Then, the computing platform filters out OTUs with the lowest occurrence, such that only those that appeared in at least 2% of the samples were retained for further analysis (e.g., 5753 OTUs from a first agriculture site location, and 4784 OTUs from a second agriculture site location). The computing platform then implemented a check step involving a Mantel test of Bray Curtis dissimilarities, in order to determine that the filtered communities represented the full local communities adequately. Then, the data was transformed to account for presence and absence factors with a conservative strategy that estimates the probability of two species co-including or co-excluding each other, at a frequency less or greater than the observed frequency if the two species were distributed independently among sites. As such, the example sub-steps of step S130 were configured to avoid varying sequencing depths and detectability bias, which was bypassed by rarefying the dataset. The example sub-steps of step S130 further implemented a conservative approach that did not rely upon correlations, was rapid, analytically stable, and did not assume a prior network structure. (However, prior knowledge of a given crop type, location, management, etc., can be readily incorporated with this method). Finally, the significant pair-wise co-inclusion and co-exclusion probabilities ($p<0.05$) were determined separately for samples from different locations, and the full groupings of positive and negative significantly-associated pairs represented the potential for interactions in complete metacommunity and/or environmental distributions.

In the example, the two groupings of positive and negative pairs (e.g., from the pair-wise co-inclusion and co-exclusion methods above) were transformed into two species matrices representing the possibility of co-inclusion/co-exclusion in the whole metacommunity. To estimate network properties in each local sample, the two metacommunity-based species matrices were subsequently further processed to generate 350 matrices containing only the species occurring in each of the individual samples. In the example, each of these matrices was transformed into a respective undirected network, where nodes represent species, and edges represent statistically significant co-occurrences/co-exclusions. For each network the example method estimated the following properties: the number of connected components, modularity, clustering coefficient defined as average transitivity, average path length and assortativity (i.e., where a larger-scale metacommunity network, considering samples from multiple locations), was punctually used to calculate the relationship between network properties in a unique large-scale continental context; proportion of co-inclusions observed out of the total number of combinations of all the OTUs in the sample; proportion of co-exclusions observed out of the total number of combinations of all the OTUs in the sample.

2.4 Methods—Model Development and Use

Step S140 recites: returning an analysis characterizing a status of the agriculture site in relation to at least one perturbation, upon processing the set of features. Step S140 functions to implement feature data as inputs, and to generate outputs corresponding to agriculture site statuses and/or responses to various perturbations, where computing platform subsystems described can implement architecture for processing features, generating network data, providing insights, with training of models by processing suitable training datasets. In particular, the emergent properties and/or other features described are not practically detectable in the mind, and are instead trained and processed by the machine learning architecture in relation to associated steps of the method 100. The analysis can be used to characterize aspects of the agriculture site in association with the perturbation(s), where the aspects can include resilience to disease risk, terroir, soil health, nutrient metabolism, yield, tissue nutrient composition, shelf-life associated with the agriculture produce, and other aspects of the agriculture site.

Figure 2:
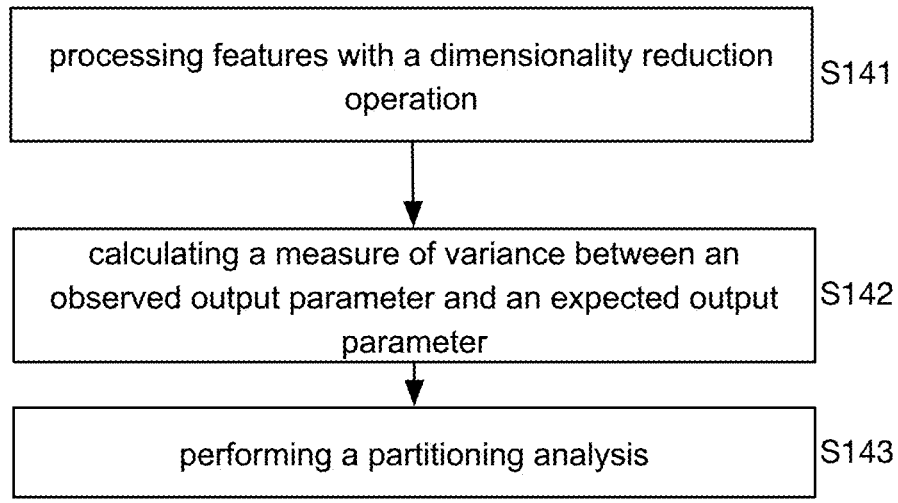
FIG. 2: depicts an embodiment of a portion of a workflow of a method for agriculture site analysis.

In one aspect, as shown in FIG. 2, a generated model can include architecture for processing features (e.g., estimates of alpha diversity, co-inclusion features, co-exclusion features, other features described above), with a dimensionality reduction operation S141 (e.g., PCA) as described above. Then, in order to evaluate the degree in which local network properties deviate from a null model expectation (e.g., based upon an expected unperturbed state), the computing platform can include architecture for processing matrices containing only the species occurring in each of the individual samples, which were randomized across the metacommunity co-inclusion/co-exclusion matrices.

The computing platform can then, as shown in FIG. 2, include architecture for calculating a measure of variance between an observed output parameter and an expected output parameter (e.g., the number of standard deviations that an observed property is from the mean of the null expected distribution, within 1000 randomizations) S142, followed by assessment if a perturbance (e.g., weather, management, applied product, etc.) had an effect on network properties (e.g., through Spearman correlations, through Kruskal-Wallis tests, etc.) as described above.

To estimate the relative contribution of a perturbation (e.g., weather, geographic location, product, etc.) and/or other characteristic related to network and organism heterogeneity of the metacommunities, the computing platform can include, as shown in FIG. 2, architecture for performing a partitioning analysis S143 using the non-metric multidimensional scaling (nMDS) two-dimension scores as the response variables. In an example, the three sets of variables were subject to a forward selection procedure, removing collinear variables, prior to their use as explanatory groups of variables. Sub-architecture of the model further included portions configured to predict the presence or absence of plant pathogens (e.g., using a curated list of crop site pathogens), by quantifying the total number of plant pathogens. Variations of sub-architecture of the model can thus be configured to process explanatory variables to generate predictions of statuses and/or perturbations to ecology of the agriculture site(s) being analysed.

In variations, the computing platform can include architecture for calculating predicted probabilities of presence of pathogens or other statuses/perturbations, by fitting variables derived from features described above (e.g., in relation to a transitivity feature, in relation to a modularity feature, in relation to an average path length, feature, in relation to a co-exclusion proportion parameter, etc.) into a generalized linear model (GLM) with a suitable distribution (e.g., a binomial distribution).

As such, architecture of the systems described in relation to step S140 can process input features and return outputs that are indicative of statuses and responses to various perturbations, which can be used in downstream portions of the method 100 in order to improve or maintain characteristics of the agriculture site(s) being analysed in a desired and/or sustainable manner.

With further training, advanced models can further be configured to process network characteristics, without knowledge of specific composition (e.g., taxonomic composition) of samples, in order to characterize aspects of the agriculture sites.

2.4.1 Models and Machine Learning Approaches

To refine the model(s), the method 100 can include generating one or more training sets of data, from samples of the agriculture site(s) and/or other samples of other agriculture site(s), in order to train the artificial intelligence (AI)/neural network (NN) model(s) in or more stages of training, to identify features of interest from various inputs. In variations, generating training sets of data can include processing raw data and/or features taken from agriculture sites with known characteristics (e.g., in relation to contextual data described above, in relation to perturbations applied in substantially controlled settings, etc.). Such training data can be tagged with associated agriculture site statuses (e.g., health statuses) and/or other information (e.g., pertaining to nature of perturbations, etc.).

In examples, training data can include tagged contextual information, which can include environmental information, geolocation information, nature of products applied (e.g., dosing, duration of application, frequency of application), pathogens present at a site, and/or other suitable information.

Figure 3:
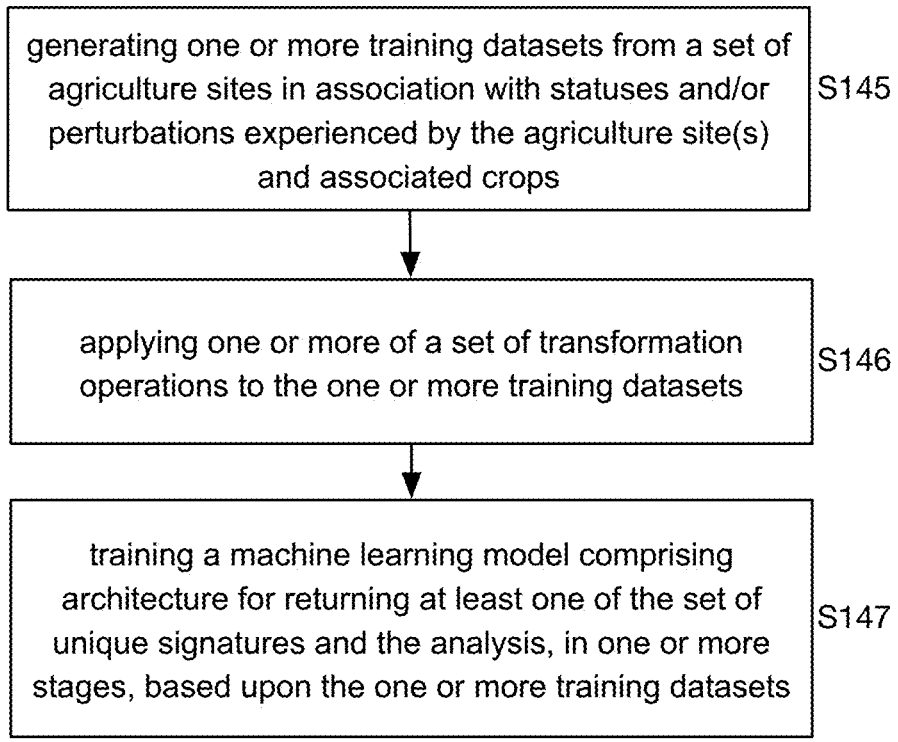
FIG. 3 depicts an embodiment of a portion of a workflow of a method for agriculture site analysis.

Training sets of data can include raw sequencing data, transformed sequencing data (e.g., according to transformation operations described above), and/or other suitable data. As such, as shown in FIG. 3, the method 100 can include: generating one or more training datasets S145 from a set of agriculture sites (e.g., sites different from those in step S110, sites overlapping with those in step S110), the training datasets corresponding to features (e.g., of emergent properties, of community properties, of taxonomic properties, of functional properties, etc.) in association with statuses and/or perturbations experienced by the agriculture site(s) and associated crops; applying one or more of a set of transformation operations to the one or more training datasets (e.g., using one or more operations described above) S146; and training a machine learning model comprising architecture for returning at least one of the set of unique signatures and the analysis, in one or more stages, based upon the one or more training datasets S147. Additional details are provided below.

For instance, in relation to generation of training datasets, the method can include generating network properties/emergent properties and other features upon samples from agriculture sites (or other sites) where statuses and/or perturbations are known. Additionally or alternatively, first training datasets can be generated from network properties/emergent properties and other features upon processing samples from agriculture sites (or other sites) known to be at baseline state. The model can be trained based upon the first training datasets. Then, the site(s) and/or associated crops can be intentionally perturbed in some manner, with subsequent sample acquisition and processing used to generate second training datasets for refining the model. This process can be repeated any suitable number of times. As such, training data can be developed in multiple stages. In relation to multiple stages of training, the method 100 can refine models based upon incorrect classification of outputs (e.g., mis-characterized statuses and/or perturbations).

Furthermore, combinatorial features (e.g., combinations features derived from one or more individual network properties, one or more community properties, one or more taxonomic properties, and/or other suitable properties can be used for training. In more detail, features may be transformed either individually or in combination before being processed by the model(s). As an example of an individual feature transformation, a feature derived from a transform of a co-exclusion feature might be used instead of or in addition to the co-exclusion feature itself. As an example, a combinatorial feature can be derived from synchronous co-exclusion of a pair of organisms and co-inclusion of a pair of organisms (e.g., where occurrence together is a feature). Additionally or alternatively, combinatorial features based upon bacteria-associated parameters and fungal-associated parameters can be used as inputs (e.g., as a unified "impact" parameter or feature).

Figure 4A:
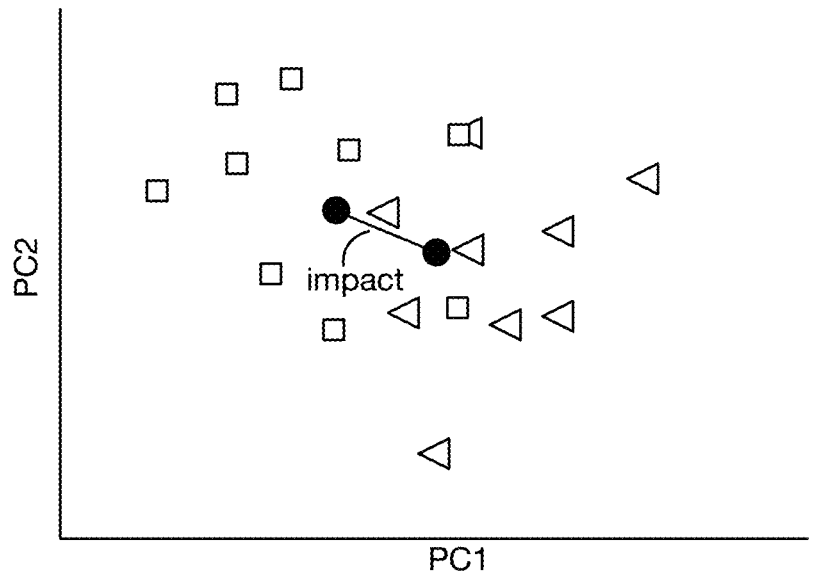
FIGS. 4A and 4B depict variations of methods for determining an impact combinatorial feature.
Figure 4B:
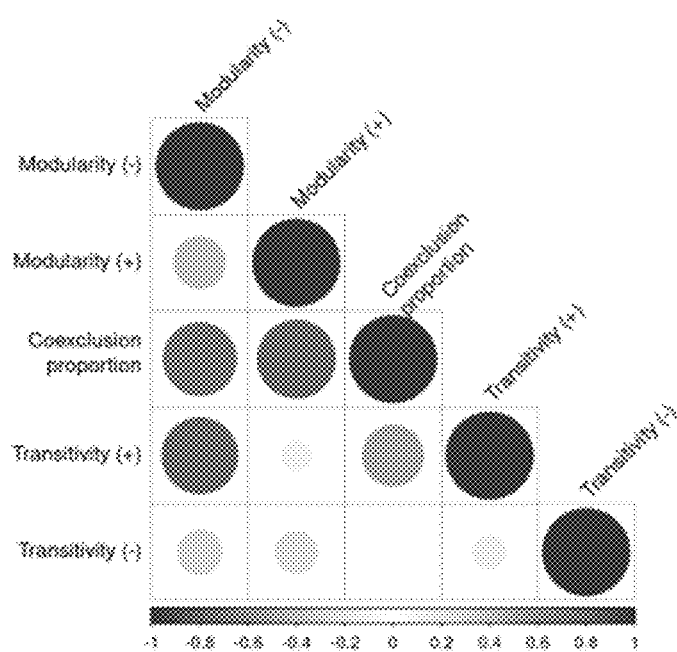

For instance, an impact parameter can be derived from the scaled dissimilarity (distance) between the network properties (e.g., 16S network properties, ITS network properties) of treated and control samples in a given location, as a measure of the effect of a given perturbation (e.g., treatment, management practice, product, etc.) on the bacterial and fungal network properties of the soil from one location. A linear regression model can be used to model the network properties, using location and timepoint only. The residuals of these models are then projected onto a 10-dimensional space using principal component analysis (PCA), retaining 83% of variation in the residuals. In more detail, a method for determining impact parameters can include: modelling network properties from samples, using desired contextual parameters (e.g., location, time point), with collection of residuals; running a PCA on these residuals and generate a multi-dimensional location for each sample; and calculating the distance between the treatment and control centroids, as shown in FIG. 4A. For each location, the impact parameter is the weighted distance between treated and control samples of that location. Impact parameter values are thus distances (i.e. non-negative), and an impact parameter value of zero means that the treatment had negligible effect on the network properties of the soil microbiome. The larger the number the larger the effect. Example correlations between properties associated with individual network parameters from which the impact parameter(s) are derived are depicted in FIG. 4B, where larger circle dimensions indicate higher degrees of correlation.

Additionally or alternatively, dynamic aspects (e.g., changes over time in features, changes in frequency between instances of respective features, other temporal aspects, other frequency-related aspects, etc.) of features derived from the samples can be used to predict or otherwise anticipate statuses. As such, models can be implemented to prevent adverse statuses of the agriculture sites to prevent root causes of failure and/or break chains of events that could lead to a cascade of agriculture site problems.

Models can be developed and trained for real-time analyses and/or historical analyses. In relation to real-time analyses, the models can be refined for rapid classification (e.g., with node reduction, with reduced thresholds, with lower confidence, etc.). In relation to historical analyses, the models can be refined for detailed classification (e.g., without node reduction, with higher thresholds for classification predictions, with higher confidence, etc.).

In embodiments, the method 100 can thus include training a model configured to process input features and return predicted characterizations of the agriculture site, wherein training the model comprises: collecting a training dataset derived from training samples, the training dataset corresponding to training samples subject to at least one of the management practice and the perturbation to the agriculture site as well as control samples without undergoing the perturbation; applying one or more of a set of transformation operations to the training dataset; and training the model with the training dataset, the model comprising architecture for returning the analysis with identification of at least one of the management practice and the perturbation, in one or more stages.

While embodiments, variations, and examples of models (e.g., in relation to inputs, outputs, and training) are described above, models associated with the method 300 can additionally or alternatively include other blocks for statistical analysis of data and/or machine learning architecture.

Statistical analyses and/or machine learning algorithm(s) can be characterized by a learning style including any one or more of: supervised learning (e.g., using back propagation neural networks), unsupervised learning (e.g., K-means clustering), semi-supervised learning, reinforcement learning (e.g., using a Q-learning algorithm, using temporal difference learning, etc.), and any other suitable learning style.

Furthermore, any algorithm(s) can implement any one or more of: a regression algorithm, an instance-based method (e.g., k-nearest neighbor, learning vector quantization, self-organizing map, etc.), a regularization method, a decision tree learning method (e.g., classification and regression tree, chi-squared approach, random forest approach, multivariate adaptive approach, gradient boosting machine approach, etc.), a Bayesian method (e.g., naïve Bayes, Bayesian belief network, etc.), a kernel method (e.g., a support vector machine, a linear discriminant analysis, etc.), a clustering method (e.g., k-means clustering), an associated rule learning algorithm (e.g., an Apriori algorithm), an artificial neural network model (e.g., a back-propagation method, a Hopfield network method, a learning vector quantization method, etc.), a deep learning algorithm (e.g., a Boltzmann machine, a convolution network method, a stacked auto-encoder method, etc.), a dimensionality reduction method (e.g., principal component analysis, partial least squares regression, etc.), an ensemble method (e.g., boosting, boot strapped aggregation, gradient boosting machine approach, etc.), and any suitable form of algorithm.

2.5 Methods—Insights and Interventions

Step S150 recites: executing an action for at least one of maintaining and improving the agriculture site, based upon the analysis. Step S150 functions to process outputs of step S140 in order to generate insights and/or execute actions that can improve productivity, correct issues, and/or increase sustainability of practices at the agriculture site(s) being assessed.

In variations, executed actions can include or be associated with one or more of: maintaining a status of an agriculture site according by providing guidance for maintaining current management statuses and/or products used; responding to an issue detected at the agriculture site(s) being assessed (e.g., in relation to pathogen presence, in relation to correcting a perturbation, in relation to adjusting application of a product at the agriculture site, implementing protective measures against environmental effects, etc.); responding to or otherwise correcting other undesired statuses at one or more agriculture sites being monitored; providing information regarding site characteristics to a manager/operator/other entity associated with the agriculture site(s); performing decision-making guidance (e.g., in relation to analyses indicative of sustainability of practices, in relation to long term effects of use of one or more products, etc.); and performing other suitable actions.

In generating recommended actions, step S150 can include returning notifications or other information derived from the analyses and other outputs of step S140 in a visual format, in an audio format, in a haptic format, and/or in any other suitable observable format, to a manager, operator, and/or other entity associated with the agriculture site(s) being assessed. As such, variations of Block S150 can include generating digital objects (e.g., in visual data formats, in audio data formats, in haptic data formats) or instructions for generating digital objects, in communication with client devices (e.g., mobile devices or other devices that are associated with a manager, operator, and/or other entity associated with the agriculture site(s)), where the client devices include visual output components (e.g., a display), audio output components (e.g., speaker), haptic output components (e.g., vibrators), and/or any other suitable components. Client devices can also include input components (e.g., keypads, touch displays, microphones, joysticks, mice, etc.) such that the managers, operators, or other entities associated with the agriculture site(s) can communicate inputs (e.g., commands) related to the generated analyses.

Additionally or alternatively, generating recommended actions can include generating control instructions for apparatus (e.g., machinery, robotic apparatus configured to traverse an agricultural site, other apparatus) configured to execute computer-readable instructions for management of the agriculture site(s). In variations, control instructions can involve instructions for controlling operation modes of one or more of: watering subsystems (e.g., in relation to water distribution through conduits and/or sprinklers to the agriculture site(s)); product delivery subsystems in communication with watering subsystems (e.g., delivery subsystems in communication with watering subsystems through fluidic components, valves, etc.); robotic crop handling subsystems (e.g., in relation to removal of pathogen-affected crop portions); robotic crop picking subsystems (e.g., in relation to automated harvesting at optimal time periods in relation to improving production, in relation to efficiency of new production generation post-harvesting, in relation to minimization of wasted product, etc.); robotic nutrient delivery subsystems (e.g., in relation to initiating delivery, in relation to stopping delivery, in relation to adjusting frequency of delivery, in relation to adjusting delivery dosages, etc.); greenhouse subsystems; temperature control subsystems (e.g., in relation to modes for controlling environmental temperature of the agriculture site, etc.); light control subsystems (e.g., in relation to modes for controlling environmental light of the agriculture site, in relation to transitioning between on and off states, in relation to light spectrum delivered, etc.); gas environment subsystems (e.g., in relation to modes for controlling environmental gas composition of the agriculture site, etc.); humidity control subsystems (e.g., in relation to modes for controlling environmental humidity levels of the agriculture site, etc.); pressure control subsystems (e.g., in relation to modes for controlling environmental pressure of the agriculture site, etc.); and other suitable subsystem(s) of the agriculture site(s). Additionally or alternatively, step S150 can include generation of control instructions for automated vehicle platforms associated with controlling vehicles associated with the agriculture site(s), with respect to surveying, management, and/or other operation modes.

Step S150 can include or be associated with executing the recommended action S151 through electronic communication with one or more subsystems described above, which functions to automatically execute recommended actions in order to reduce operator workload in relation to agriculture site management. Executed actions can include or be associated with one or more of: maintaining a status of an agriculture site according by providing guidance for maintaining current management statuses and/or products used;

responding to an issue detected at the agriculture site(s) being assessed (e.g., in relation to pathogen presence, in relation to correcting a perturbation, in relation to adjusting application of a product at the agriculture site, implementing protective measures against environmental effects, etc.); responding to or otherwise correcting other undesired statuses at one or more agriculture sites being monitored; providing information regarding site characteristics to a manager/operator/other entity associated with the agriculture site(s); performing decision-making guidance (e.g., in relation to analyses indicative of sustainability of practices, in relation to long term effects of use of one or more products, etc.); and performing other suitable actions, as described above in embodiments, variations, and examples of agriculture site management control and notification/report delivery.

2.5.1 Example Insights and Interventions with Respect to Fungal Biodiversity

In one example, analyses returned by an example of the method(s) described above indicated that features processed from emergent properties associated with fungal biodiversity of the soil ecosystem of an agriculture site informed insights and actions pertaining to soil health, due to involvement of fungal organisms in ecosystem services (e.g., organic matter transformations, nutrient cycling, biocontrol agents, soil respiration), and fungal-plant interactions (i.e., through bioactive phytochemicals, pathogen occurrence, and effects on soil fertility.

In particular, in one example related to samples from the soil rhizosphere, features were generated in relation to niche differentiation factors, where niche differentiation facilitates the coexistence of functional guilds, modulating the regulation of soil carbon dynamics. As another example related to samples from the topsoil, features were generated in relation to the abundance of antibiotic-resistance genes, where outputs of the model indicated higher fungal abundances through competitive interactions. Such insights from the trained model(s) were then used to guide monitoring of the agriculture site and management of crops, with detection of stressful conditions (e.g., risk of drought, other environmental factors, antibiotic resistance, etc.).

Expanding upon this example, co-inclusion/co-exclusion networks generated in variations of steps S130 and S140 above further merged metacommunity-inferred associations into each of the local communities, which enabled estimation of network properties in all the local communities within the metacommunity to provide insights into local microbial ecosystem aspects of agriculture sites. Generation of such co-inclusion/co-exclusion networks with metacommunity and local level analyses further enabled direct comparison among network properties of individual samples, even in the absence of common taxa among them, which were used to guide actions to adjust management practices (e.g., in relation to conventional practices, in relation to organic practices, in relation to biodynamic practices, etc.) at agriculture sites. In related examples, returned outputs of models configured to process emergent property features and/or other features were used to control subsystems for implementing adjustments to conventional management practices, organic management practices, and biodynamic management practices. In still related examples, returned outputs of models configured to process emergent property features and/or other features were used to control subsystems for transitioning management practices between conventional management practices, organic management practices, and biodynamic management practices in order to produce desired results (e.g., in relation to productivity measures, in relation to sustainability measures, etc.). Example actions relate to halting use of mineral nitrogen fertilizers, synthetic pesticides, and phytosanitary products; promoting use of compost-based fertilization and cover crops to enhance soil fertility and microbial diversity by improving the composting process.

In further detail, upon processing a features of a dataset of 350 vineyard soil samples from two geographic locations, examples of model architecture implemented in relation to step S140 described above returned insights characterizing fungal communities having random to small-world network arrangements with differential levels of niche specialization, where some of the network properties studied were strongly correlated, defining patterns of ecological emergent properties that are influenced by the intensification level of the crop management. As such, features characterizing different ecological strategies that fungal communities adopt in face of different levels of farming intensification and management practices were used to assess agriculture site statuses (e.g., in relation to health statuses of soils, in relation to responses to external stresses such as global change, pathogens invasion, etc). Characterizations include indications of more generalist-collaborative biota in the soils with less anthropogenic activity, and a more niche-specialized biota in those soils with more intensified management. Further characterizations returned by trained models indicated the influence of farming practices on the richness of fungal plant pathogens in the soil, where conventional vineyards showed the lowest values, with the higher co-exclusions proportion in the network appearing to be linked with the lower values of pathogen richness. Such outputs were used to identify, modulate, and/or transition between: low-intervention practices (from organic to biodynamic approaches) that promoted densely clustered networks (e.g., an equilibrium state based on mixed generalist-collaborative communities), conventional management practices that promoted highly modular niche-specialized and low clustered communities (e.g., with a higher degree of selection and a greater degree of co-exclusion. As such, the models were configured to capture and characterize the relationship between network properties in local fungal communities in relation to impact of farming practices, independent of location, thereby enabling such methods and models to have global impact in crop production strategies (e.g., in the wine industry, in the agri-food industry, in the beverage industry, etc.).

Detailed aspects of insights derived from models associated with the example are provided in Sections 2.5.1.1 through 2.5.1.4 as follows:

2.5.1.1 Fungal Community Assembly in Vineyard Soils is Affected by Biogeography and Management Factors In relation to the agriculture sites (i.e., vineyards) being analysed, model assumptions were based upon vineyards as stabilized and bounded ecosystems (e.g., due to long histories of preservation, management, and exploitation within the same soil), where human intervention through different types of farming practices drives fungal community composition and structure impacting vine health and wine fermentation performance.

Figure 5:
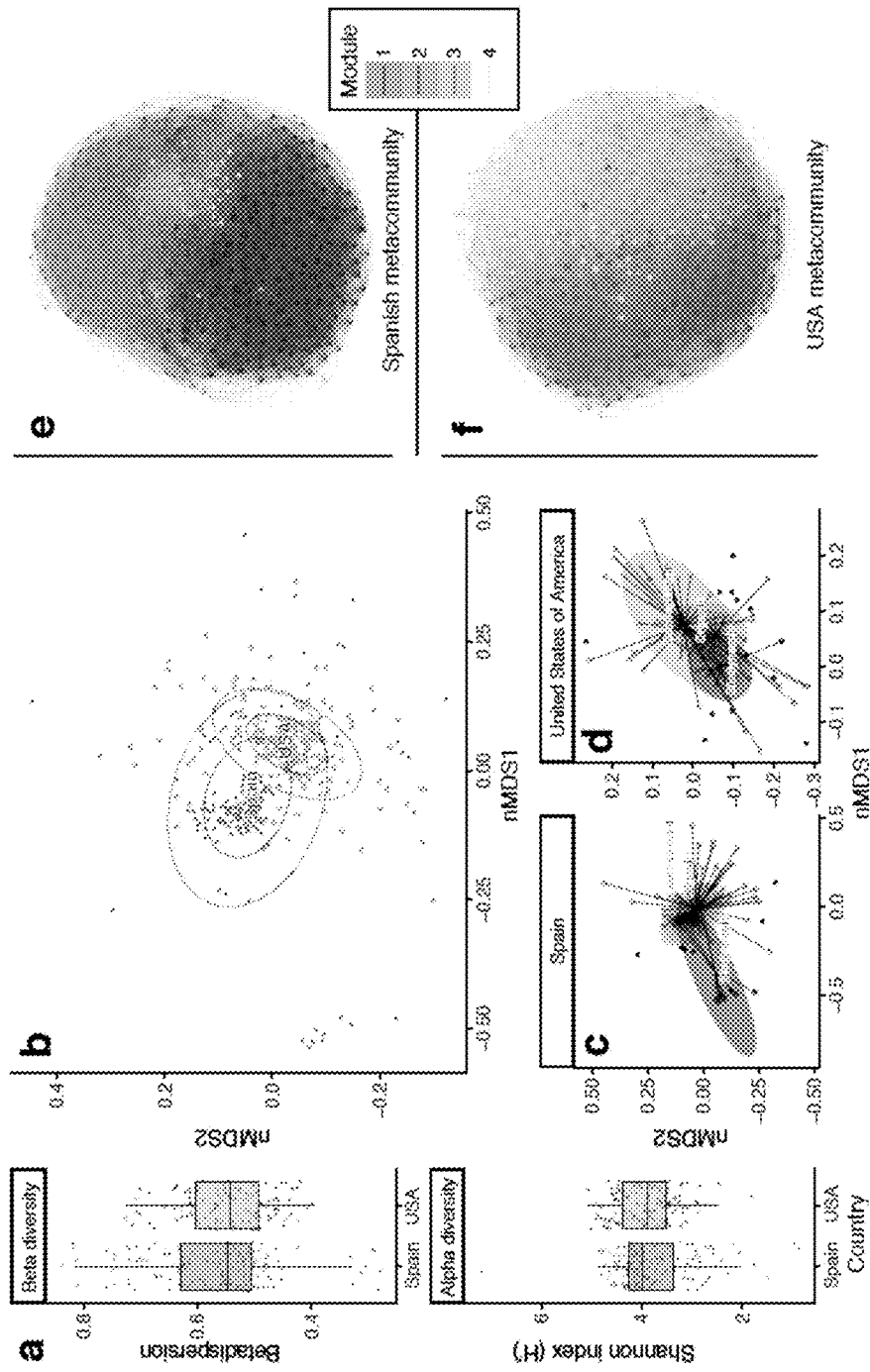
FIG. 5 depicts outputs of a first example of a model for agriculture site analysis.
Figure 6:
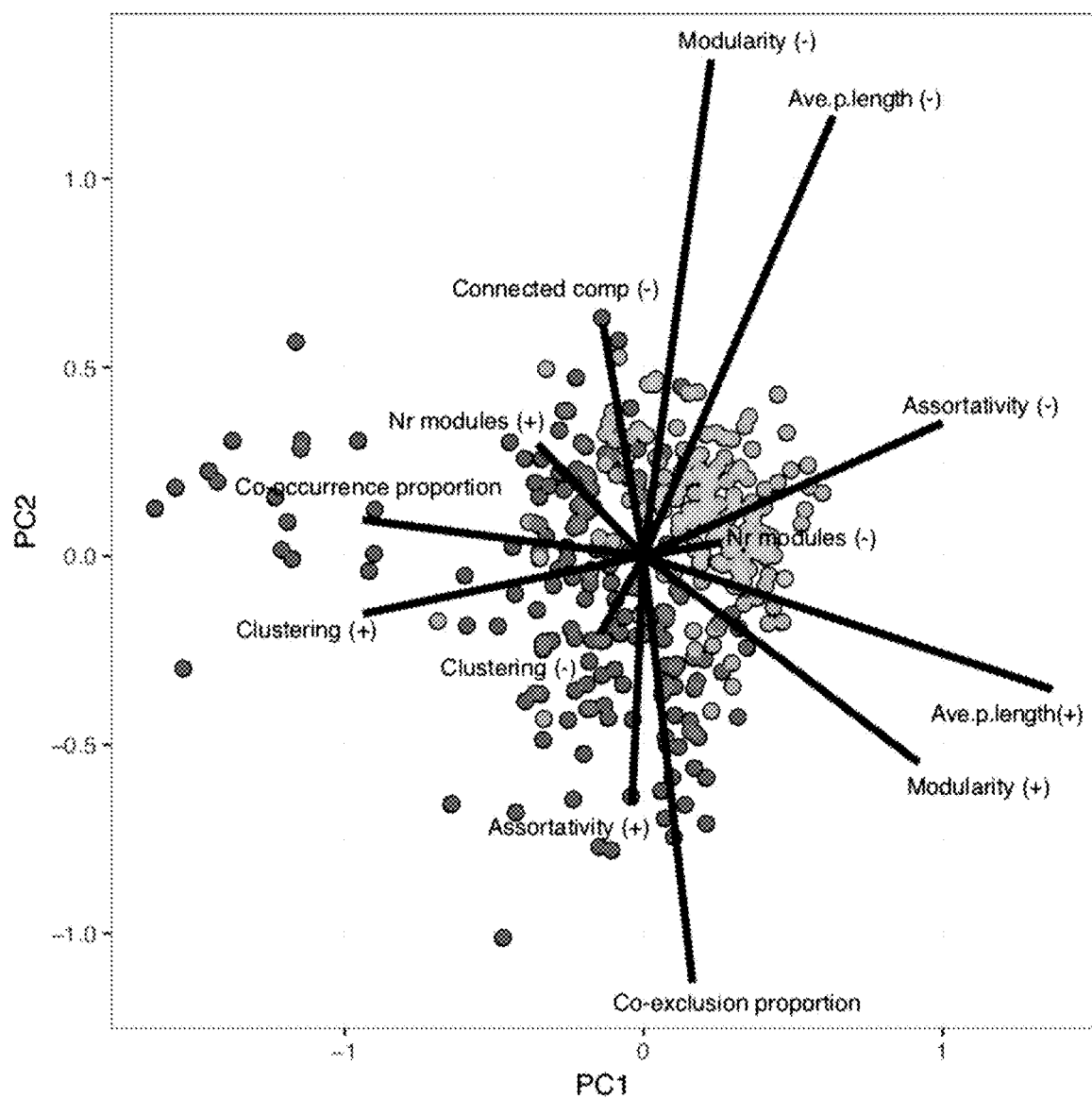
FIG. 6 depicts PCA outputs of network and emergent features associated with a method for agriculture site analysis.

FIG. 5 (a, top left) depicts similar alpha-diversity (H') and beta-diversity (i.e., beta dispersion) ranges for samples acquired from a first location (i.e., the U.S.) and a second location (i.e., Spain), with similar proportions of dominant fungal classes across locations. However, the non-metric multivariate ordination of OTU composition showed origin-dependent clusters, as shown in FIG. 5 (b, top middle), where such clusters were also differentiated in the multivariate ordination of network properties as shown in FIG. 6.

As such, fungal community composition and network properties could be used to determine corresponding farming practices of a set of farming practices (e.g., conventional, organic, and biodynamic) for vineyard management, as shown in FIGS. 5 (c, bottom left) and 5 (d, bottom right).

The model also indicated that the second location (i.e., Spain), which has the largest organic grape cultivar worldwide had an undetectable fungal diversity difference between organic vineyards and conventional vineyards, as shown in FIG. 5 (c, bottom left). However, at the first location (i.e., the U.S.), which has a smaller organic production, type of management had a significant effect on the soil fungal diversity, with respect to an intermediate management type between conventional and biodynamic managed vineyards, as shown in FIG. 5 (d, bottom right). Given these different country-defined sample clusters, both datasets were analysed separately, and two different metacommunities were defined based on co-inclusion/co-exclusion patterns: one for samples of the first location, and one for samples of the second location, as shown in FIGS. 5 (e, top right) and 5 (f, bottom far right). The processing of features associated with co-inclusion metacommunity networks by operations described above further highlighted a single connected component with high modularity across locations, high clustering coefficient across locations, variable assortativity across locations, short average path length across locations, and a higher observed proportion of co-inclusion and lower co-exclusion edges out of the total combinations, across locations.

Figure 7:
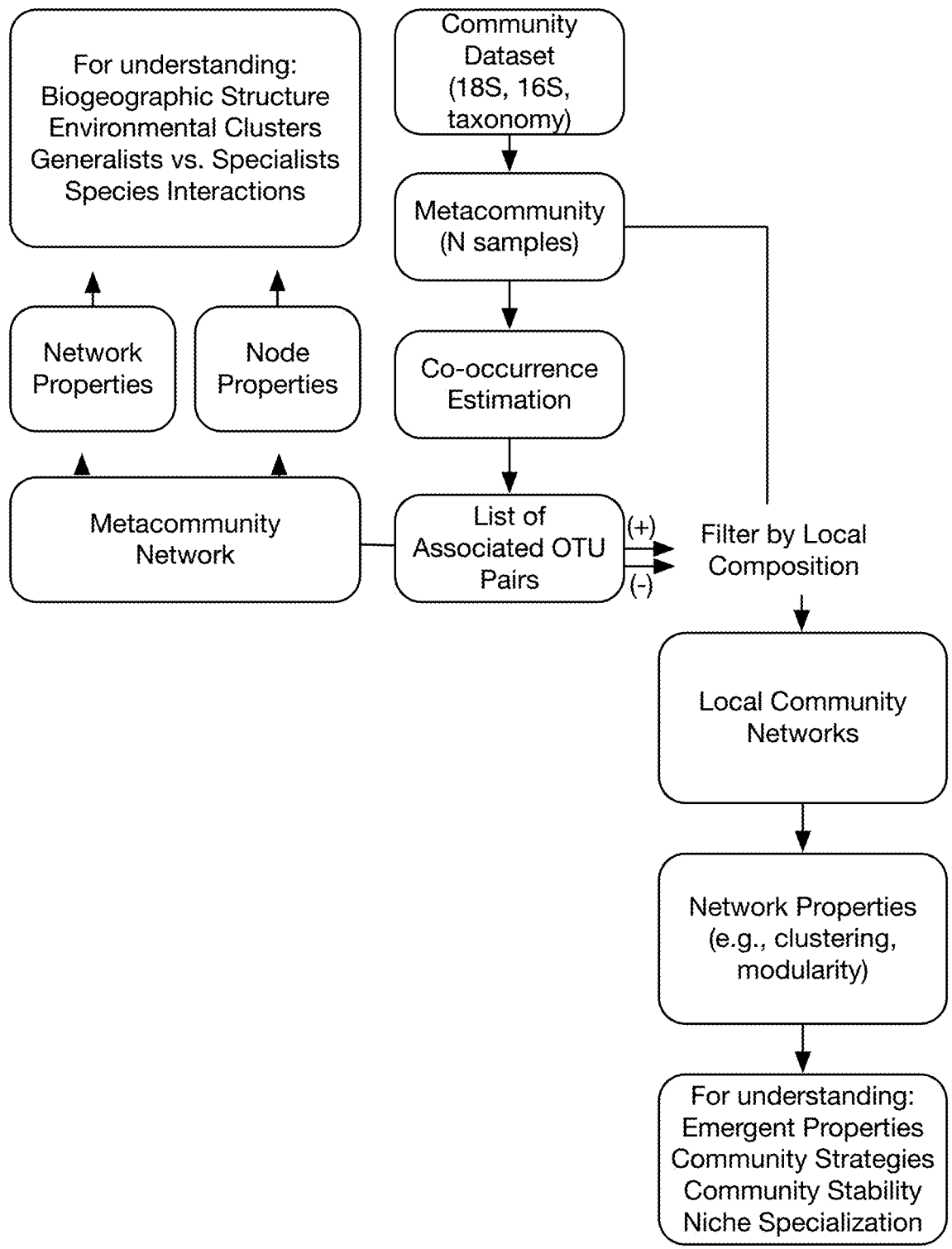
FIG. 7 depicts a flow of a process for agriculture site analysis.
Figure 8:
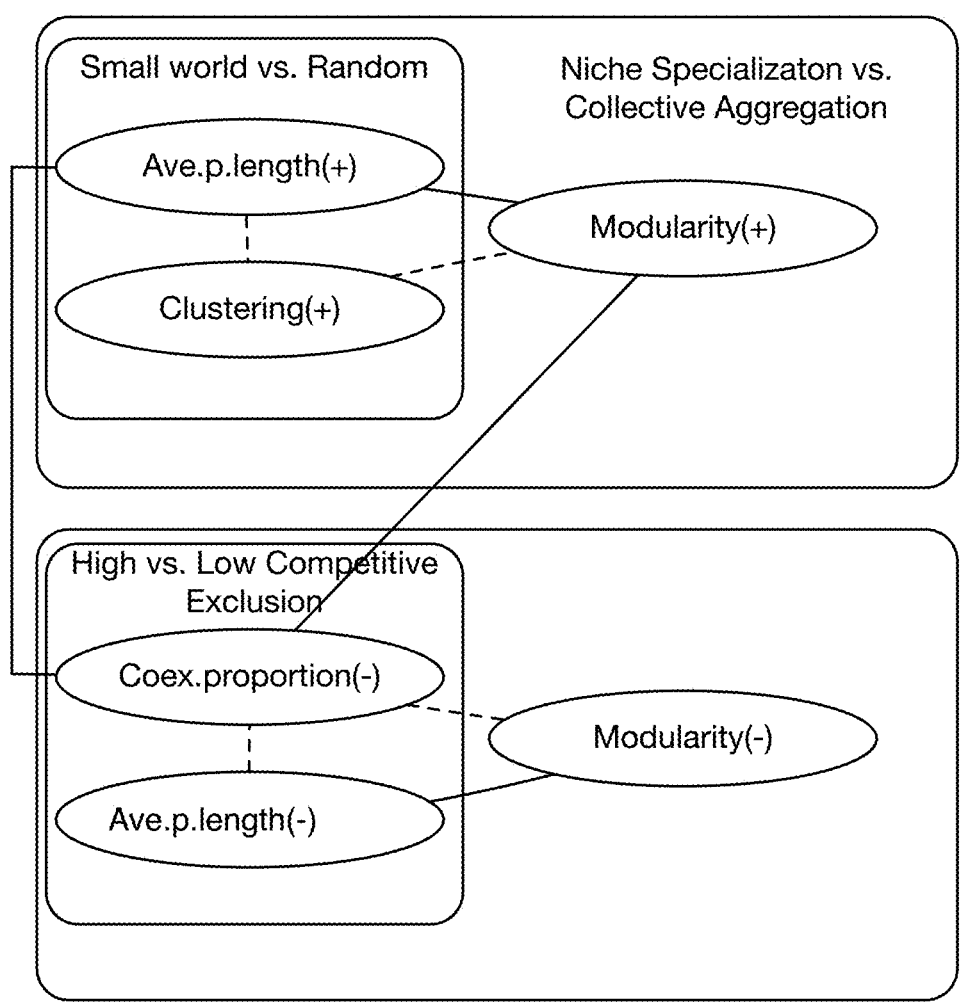
FIG. 8 depicts correlations between features for agriculture site analysis.

2.5.1.2 Climate, Geography and Local Network Properties Explain the Fungal Metacommunity Structure For the purpose of providing improved structural and mechanistic characterizations of features of the agriculture sites, network properties and emergent properties were generated from samples, thereby characterizing each local composition of microorganisms individually, as shown in FIG. 7. In more detail, local network properties displayed values having wider ranges than the overall value of the metacommunity networks of co-inclusions and co-exclusions, as shown in Table 1 of APPENDIX A. Despite the geographic differences, most of the network feature values had similar relationships in the two metacommunities, as shown in FIG. 8, but also when merging the two metacommunities into a single large-scale continental dataset. Features thus functioned as biomarkers of agriculture site statuses and characteristics, which was used to develop models associated with the method.

To evaluate the relative and combined relationships between community assembly and one or more of: geography, weather and network properties, the model implemented a partitioning analysis in two metacommunities (e.g., associated with the U.S. and Spain). Different community arrangements from each metacommunity/location were usable as biomarkers for assessing effects of meteorological factors, geography, and network properties (from lower to higher variation explanatory power. In more detail, emergent properties captured responses to different perturbations (e.g., variability due to weather in relation to axis of wind speed, in relation to altitude, in relation to temperature, in relation to cloud cover, in relation to geography, in relation to soil organic matter, in relation to pH).

2.5.1.3 Network Properties Understood as Emergent Properties are Biomarkers of Ecological Mechanisms and Environmental Filters FIG. 8 depicts a contextualization of local network properties and their relationships as emergent properties. Local network properties were first classified according to their relationships. Then, a principal Components Analysis (PCA), showed that co-inclusion-associated features and co-exclusion-associated features explained a significant portion (e.g., 54%) of the variance: the first axis (36%) correlated to properties based on co-inclusions (+), and the second axis (18%) to properties based on co-exclusions (−). Out of the properties based on co-inclusions, the strongest association was an inverse relationship between clustering coefficient and average path length, as shown in FIG. 8, indicating degree of connection density in the networks, and thus the degree of association between nodes. This relationship shows a gradient between two alternative situations, which can be interpreted as a random network (i.e., low clustering, high path length) or a small-world structure (i.e., high clustering, low path length). These two network properties were thus processed as an ecological emergent property, providing information about how the actions in one part of the community affect others, (e.g., in small-world networks, random loss of species is unlikely to affect the overall properties of the network, implying a degree of overall resistance towards potential perturbations). In this regard, a densely connected network of co-inclusionss can represent a well-integrated collaborative fungi community, where its organisms could have cooperative activities (e.g., as facilitation, syntrophy, and/or cross-feeding), and where the loss of one organism may not affect community functionality and hence not be detrimental. However, in a low clustering situation, a seemingly random configuration can reflect a different soil situation as shown by a relationship with another network property:modularity.

Modularity indicates the degree of separation of network modular components (e.g., a fraction of nodes within the network have more edges among each other than with other fractions of nodes in the network). In processing features of the model, there was an inverse relationship between the clustering coefficient (+) with modularity (+), as shown in FIG. 8. Considering the previous interpretation of densely connected networks being those with fungi preferring the same environmental conditions, the alternative situation of loosely connected networks can be indicative of communities that have adaptations to different environmental conditions, that are filtered by multiple gradients, or that harbour different specialized functional niches. Evaluation of such a situation can be based upon assessment of completeness of the main metacommunity modules in the local samples, where network modules are often indicators of the main environmental niches. Variability in the ranges of maximum temperature for the fungi in each module were observed across sample locations, as shown in FIG. 9 (a, top left) and FIG. 9 (b, top right).

Figure 9:
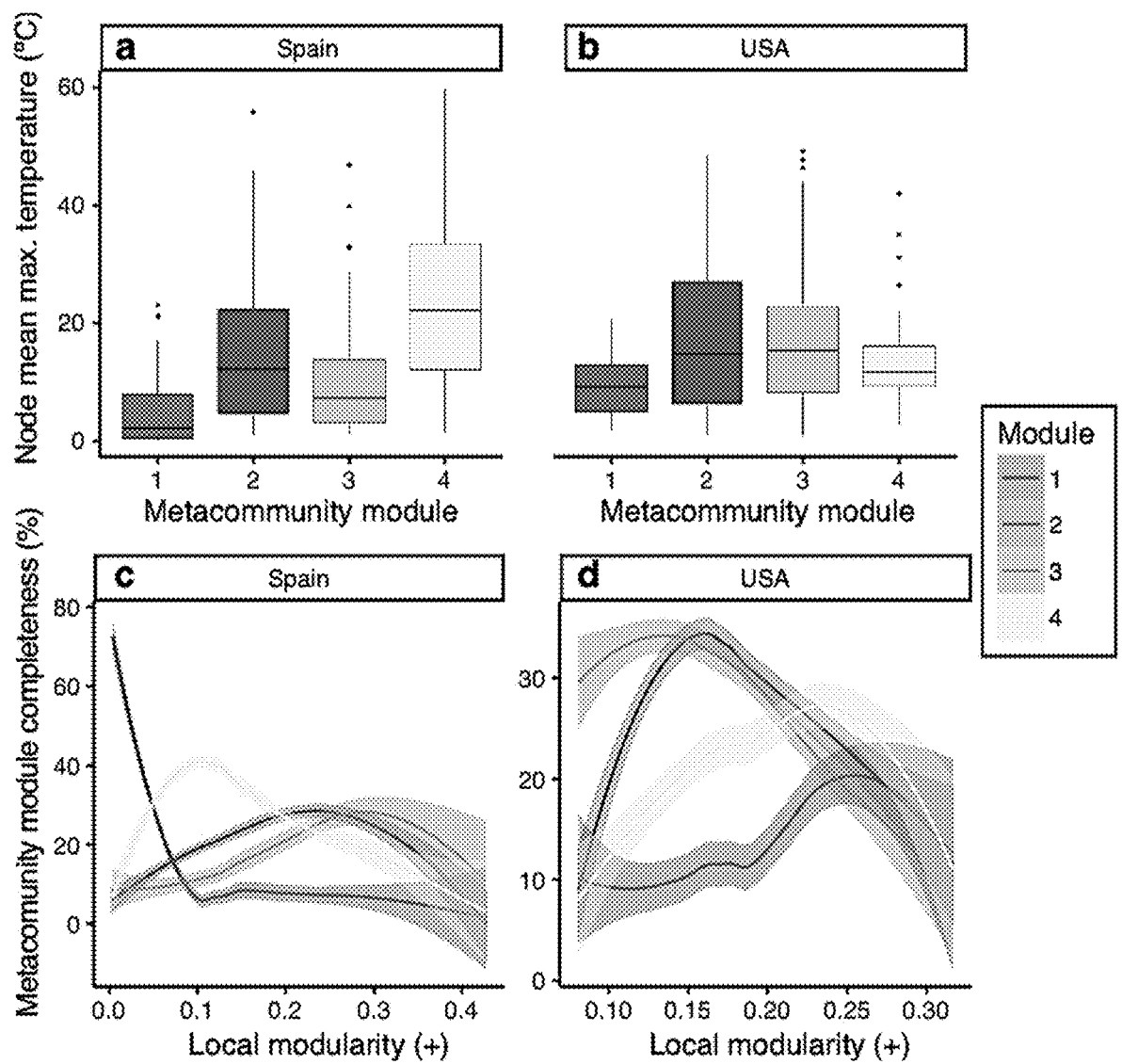
FIG. 9 depicts outputs of a model with respect to meta-communities, modularity features, and environmental effects, in association with a method for agriculture site analysis.
Figure 10:
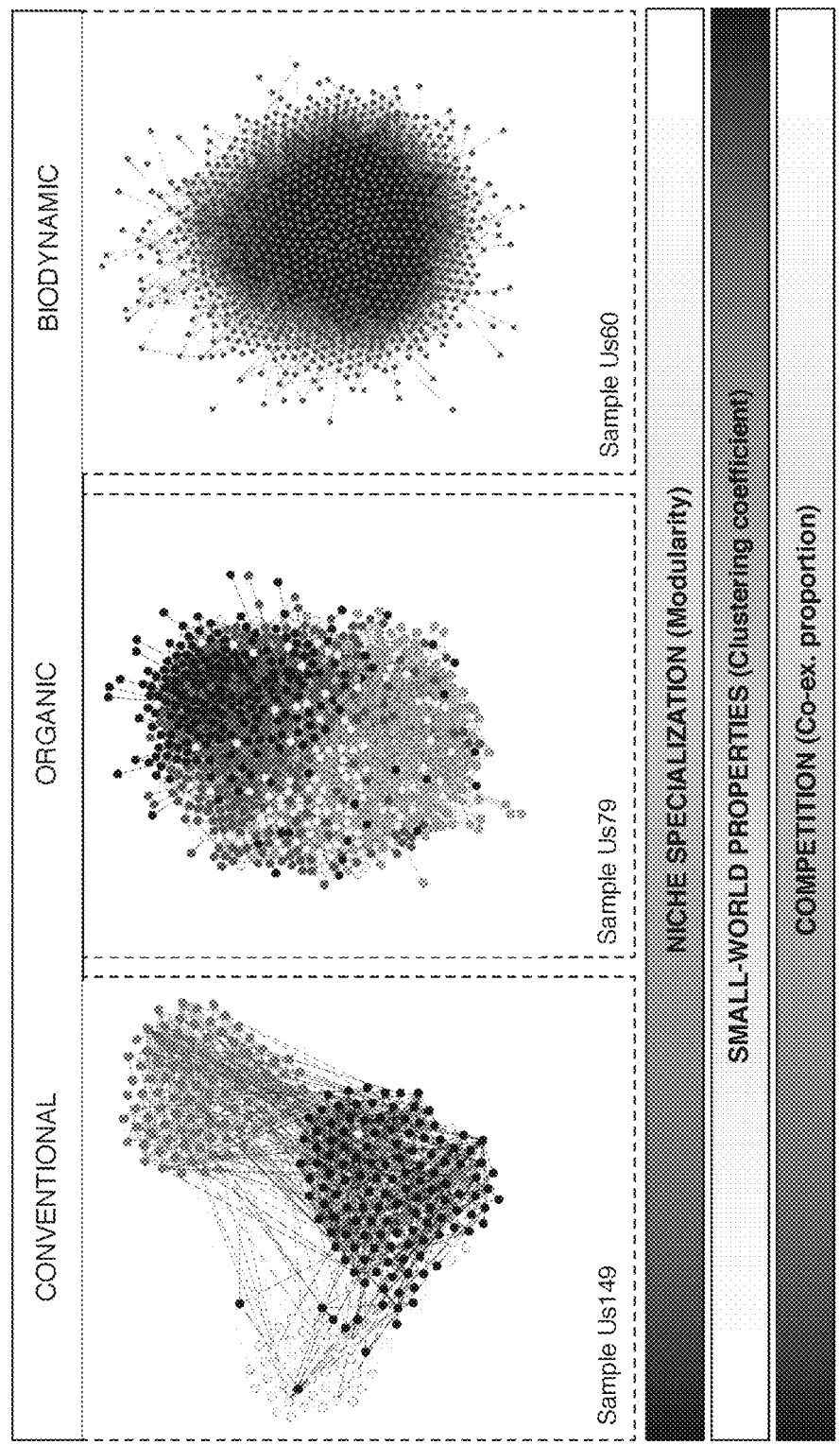
FIG. 10 depicts network effects of various management practices in association with a method for agriculture site analysis.

In processing the local modularity values in terms of niche specialization, the model indicated that each local community has different completeness of each of the modules of a particular location, as shown in FIG. 9 (c, bottom left) and FIG. 9 (d, bottom right), with variation according to the modularity value. For example, in the first location (i.e., the U.S.), modules 2 and 3 have their completeness maximums at lower local modularity values, while modules 1 and 4 have higher values at higher modularity values. At the highest modularity values, regardless of the module completeness trends, communities tend to have a bigger mix of the community modules, therefore, having a higher degree of specialized fungi, hence, increased niche specialization. Indeed, the modules in which completeness peaked at lower local modularity generally coincided with those that had higher ranges of maximum temperature, in both locations. The fact that communities have OTUs distributed across a wide range of temperatures is relevant, since drought-resistant fungi control soil organic matter decomposition and its response to temperature fluctuations. Therefore, the presence of fungi capable of thriving in broader temperature ranges, can indicate a benefit to soil health, according to the model, thereby promoting associated management practices. Together with clustering, local modularity thus has a clear ecological significance. The model further showed that mycobiomes from soils can be densely connected with low niche specialization, which can indicate fungal communities capable of responding holistically and consistently towards environmental gradients (i.e., temperature, as shown in FIG. 9 or whose members take advantage of metabolic by-products by cross-feeding or facilitation. Conversely, loosely connected networks with higher niche specialization, may indicate a mix of fungal clusters independently specialized to react differently towards a different environmental perturbation or environmental gradients, as shown in FIG. 10. However, their functional capabilities or ranges of reaction may be limited, as indicated in outputs representing a decreased completeness of the metacommunity modules or a reduced temperature range of their members, as shown in FIG. 9.

Niche specialization (or partitioning), is also one of the main strategies that organisms can pursue to survive over time in highly competitive environments, where competition is central in regulating community assembly over time. Due to its importance, features associated with proportion of co-exclusions were processed for assessment as biomarkers indicative of competition, through the use of local networks rather than metacommunity networks. Assessment of co-exclusions was based upon an assumption that respective pairs of OTUs occurred together less than expected at random. In metacommunities, these segregated pairs can indicate different niche specialization (e.g., groups of OTUs that are specialized to a particular environment and cannot thrive elsewhere), different geographic locations (e.g., a physical dispersal barrier that impedes OTUs to coincide in a particular sample), or competitive processes (i.e., antifungal and toxin production, or differences in resource-use efficiency). The estimated co-exclusions were attributed to a mix of various perturbations mentioned above; however, in the local networks estimated, it was unlikely that a co-exclusion in that community is the consequence of a dispersal difference, and since each sample has a single full set of environmental characteristics, co-exclusions in a sample can only exist if: (a), the local community has territorial niches assigned and/or (b), the local community has different OTU groups adapted independently to environmental or functional niches. The model outputs indicated that highly modular co-inclusion networks (with modularity interpreted as niche specialization) sustain a higher proportion of co-exclusions, which can indicate both increased competition processes and stronger niche separations. Furthermore, in the case of fungi, the specialization of functional guilds represents part of the local co-exclusions observed. This can indicate that fungi may be competing for the same limiting resource through interference competition (such as in mycorrhizal fungi vs saprotrophs), thus affecting soil carbon dynamics.

Thus, the model was configured to evaluate three network properties based on co-inclusions and co-exclusions to assess part of the ecology of local fungal communities. Clustering coefficient, modularity, and the proportion of co-exclusions can thus be understood as an internal community mechanism between the effect of the environment and the influence in ecosystem processes that may ultimately define soil health, which can guide management practices and use of products.

2.5.1.4 Farming Practices Determine Fungal Community Structure and Emergent Properties The environment affects fungi at the community level, displaying a consequence in emergent properties, which in turn are indicative of broader ecosystem processes. Moreover, in various agriculture sites (e.g., vineyards), the soil environment, which triggers community responses, is partially shaped by human activities. The example models implemented indicated that management strategies (e.g., conventional v.s. biodynamic approaches) affect network properties of fungal soil communities, similarly in various locations (e.g., U.S., Spain), which can be used to guide management practices. We observed that soils under a biodynamic management had higher clustering coefficient (+), lower modularity (+) and lower co-exclusions proportion than the conventionally managed soils, with organic managed samples tending to show intermediate values between conventional and biodynamic samples. Biodynamic-farmed vineyards showed microbial communities closer to: i) small-world networks (higher clustering coefficient (+)); and ii) mixed (low niche partitioning) communities (lower modularity (+)). Properties which are related with enhanced systems homeostasis and to higher resistance towards species removal and perturbations. Conversely, conventionally managed vineyards were associated with low clustered, highly modular fungal networks with a larger proportion of co-exclusions compared to other management types, where increased intensification practices reduced fungal network connectivity. Use of punctual fertilization programs with high doses of specific nutrients, as in conventional farming, can drive a metabolic specialization leading to an arrangement of niches, in contrast to the more densely connected communities observed under biodynamic management. Thus, features of the model can be used to execute actions for adjusting management of the agriculture site(s). Ultimately, biodynamic management can lead into higher quality grapes in vineyards than conventional managements, with organic practices showing an intermediate effect, based on soil fertility, nutrient availability, enzyme activity, and earthworm abundance. Outputs of the model(s) indicated that communities with lower modularity (+) had higher completeness of modules that were associated with wider temperature ranges. According to the higher clustering coefficient values and lower proportion of co-exclusions under biodynamic management, recommended management practices could thus sustain community resistance towards, at least, temperature fluctuations.

Figure 11:
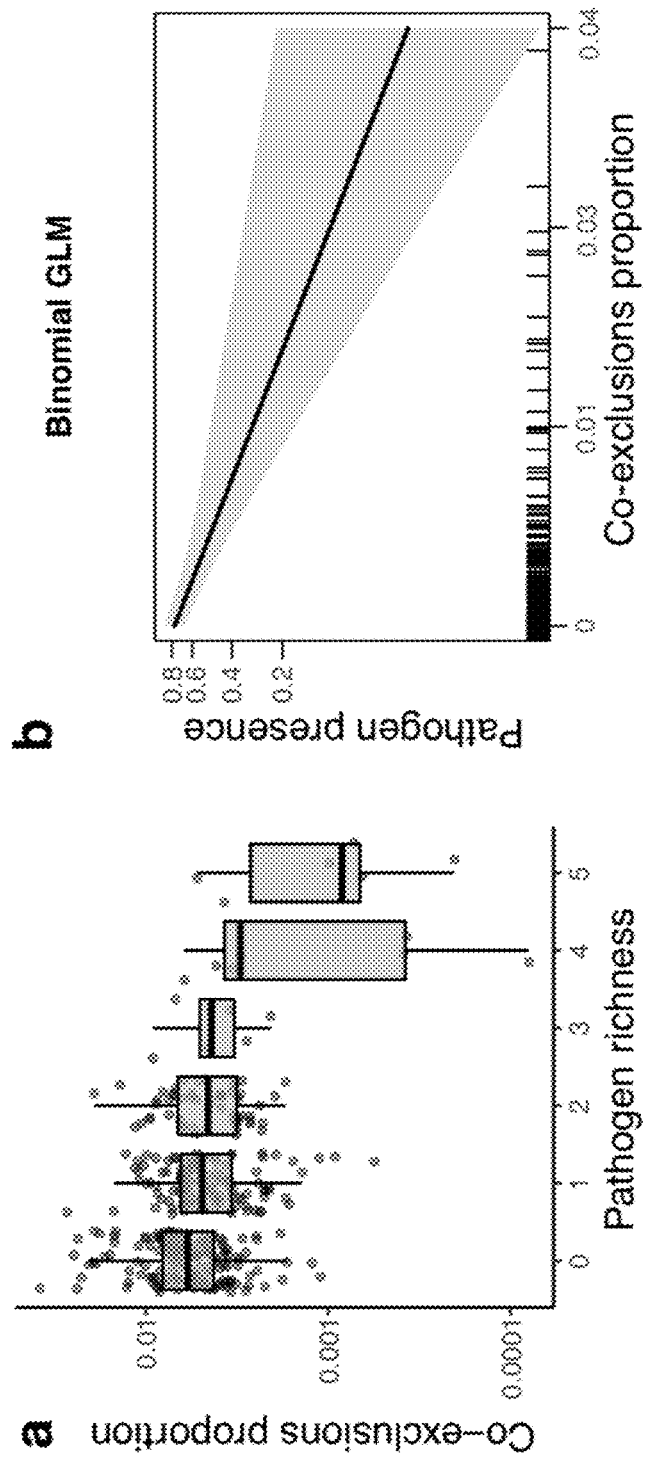
FIG. 11 depicts outputs of a model with respect to relationships between pathogens and co-exclusion proportions.

Because the assessment of fungal biodiversity as soil health indicators cannot be limited only to the determination of diversity indexes, a combination of network properties generated according to methods described is a useful approach to understand soil health. However, diversity indexes may still be useful, as outputs of the model(s) indicated that alpha diversity (H') is higher in the communities with a lower modularity and a lower proportion of co-exclusions than sparsely connected communities ($r=-0.41$, $p<0.001$), indicating that communities with the highest diversity may have presumably higher resistance towards perturbation and would tolerate wider temperature variations. In parallel, the co-exclusions proportion was associated with lower plant pathogen richness ($r=-0.28$, $p<0.001$), as shown in FIG. 11 (a, top left). A linear model implemented predicted that at the lowest co-exclusion proportion values (such as those from biodynamic and organic managements) corresponded to the probability of the presence of a plant pathogen being elevated to 80%, as shown in FIG. 11 (b, top right). Given that organic and biodynamic managements may use tillage systems to compensate the reduction/absence of chemical fertilizers and phytosanitary products, it is understandable that under organic and biodynamic management pathogen presence may be more likely.

Supplementary data tables are provided in APPENDIX A.

2.5.2 Example Insights and Interventions with Respect to Soil Microbial Composition and Action of Biostimulants In another example, models were configured to evaluate the effect of a microbial inoculant (e.g., *Bacillus subtilis* strain QST 713) on crops (e.g., potatoes), and to explore its potential relationship with crop yield. For this, we implemented approaches described above to assess the bacterial and fungal soil biodiversity in samples from potato soils, distributed over different time points—before planting (T0), one (T1) and two (T2) months after planting, and after harvest (T3)—and three different geographical regions. Model outputs indicated that the microbial inoculant applied had a significant effect over the bacterial and fungal communities assessed, but preserved the native communities without causing a detectable long lasting effect on the alpha- and beta-diversity patterns after harvest. Specific taxonomic groups, and the structure of the fungal and bacterial communities (e.g., measured by changes in co-inclusion and co-exclusion networks of these communities) changed after inoculation of the biostimulant. Information about the application of the microbial inoculant and considering microbiome composition and structure data was further used to train a Random Forest model to estimate if a soil sample came from a low or high yield block with relatively high accuracy, concluding that the structure of fungal communities is a better estimator of potato yield than the structure of bacterial communities. The methods described here can be replicated to predict yield in any other crop, and to evaluate the effect of any Ag-input product or other product (e.g., applied to soil, seeds, foliage, etc.) in the composition and structure of the soil microbiome.

In more detail, soil and rhizosphere samples were collected over three regions at 4 different time points: before planting and/or treatment (T0), one month after planting (T1), 2 months after planting (T2) and at harvest (T3). From each time-point, treated and untreated samples were collected, Bulk soils were sampled from cores at the topsoil (2-4 in deep). Samples were collected across different locations for each field and the composite was submitted for analysis, in order to achieve a more homogenized sampling reducing the effect of microbial variability. Treatment included application of a bacterial suspension solution (e.g., *Bacillus subtilis* QST 713) on each crop (e.g., potato) immediately before planting in the soil as an in-furrow application.

After collection, samples were immediately sent for molecular analysis, with DNA extraction was performed according to methods described above. To characterize both bacterial and fungal microbial communities associated with bulk soils and rhizosphere samples, the 16S rRNA and ITS marker regions were selected. Libraries were prepared following the two-step PCR Illumina protocol using custom primers amplifying the 16S rRNA V4 region and the ITS1 region. Sequencing was conducted using pair-end sequencing (2×300 bp). The bioinformatic processing of reads included the merging of forward and reverse paired reads to create robust amplicons, using a Vsearch algorithm with minimum overlaps of 100 nucleotides (nts) and merge read sizes between 70 and 400 nts. OTU clustering was performed at 97% sequence identity, followed by quality filtering through denovo chimera removal using the UCHIME algorithm. Taxonomic annotation was performed using the SINTAX algorithm, which uses k-mer similarity to identify the top taxonomy candidate, after which we retained results where the species level had an score of at least 0.7 bootstrap confidence. The SILVA database version 132 and UNITE database version 7.2 were used as taxonomic references.

Features were then generated as follows:

Alpha- and beta-diversity: Exploratory analyses of 16S and ITS OTU counts were conducted separately. Alpha- and beta-diversity were analyzed using OTU counts. Alpha-diversity metrics (e.g., Shannon and richness) were calculated and plotted across all covariates available. For beta-diversity, the model(s) implemented Kruskal's non-metric multidimensional scaling in conjunction with Aitchison distances. Relative abundances for OTUs as well as annotations at various taxonomic levels (genera, families, etc.) were used in the analyses.

Differential abundance: For all subsequent analyses, the zero counts in the data were replaced. Valid values for replacement were calculated under a Bayesian paradigm, assuming a Dirichlet prior. Non-zero values were then adjusted using architecture of the model to maintain the overall composition. Differential abundance determination was carried out by the model, and for each OTU, the fold change attributable to the treatment across different times (e.g. T0 to T1) was calculated.

Local network properties: Meta-community networks were built for 16S and ITS data separately using methods described above. The model was configured to return a metacommunity network of all samples analysed by estimating the co-inclusion and co-exclusion that would occur solely by chance for all possible OTU pairs, and then selecting OTU pairs that occurred significantly more than expected by chance to create the co-inclusion networks. Similarly, those that occurred significantly fewer times than expected by chance constitute the co-exclusion network. Local networks (single sample-level) were calculated by subsetting the metacommunity network for OTU pairs detected in each sample, and estimating a local network. Network properties were then returned, and processed to generate emergent properties as described above.

Yield model: Yield data was processed using medians and interquartile ranges (IQRs). Wilcoxon rank sum tests were then performed on these yield data. The model architecture was constructed as follows: The OTU counts were transformed using the centered log-ratio (CLR) transformation. CLR-transformed 16S and ITS data were jointly projected onto 70 principal components. Yield was modelled as the outcome of these 70 principal components, along with network properties, location and treatment, using a probability forest. Since the yield is a constant variable for all time points within a location, the yield was converted to a categorical variable ($\leq 30$ t/Ha, $>30$ t/Ha). The threshold for this division, 30 tonnes, was set at a zero probability density point for the bimodal distribution of yield. The samples (e.g., all T0 through T3 samples with corresponding yield data) were split into training and test dataset. Variable importance for each variable in the model was calculated using the Gini index. Among the 70 principal components of the microbiome included in the model, the ones with the highest importance in the probability forest were selected for further analysis. The loadings of these principal components were clustered using an unsupervised hierarchical clustering algorithm to visualize some of the most influential OTUs' impact on these principal components.

Outputs of the models associated with relationships between features and applied products are further described in the following sections:

2.5.2.1 Geography and Phenological Stage Drive the Soil and Rhizosphere Microbiome Composition of Potato Crops Returned outputs of the model(s) indicated clear population dynamics occurring from T0 (before planting) to T1 and T2 samples (1 and 2 months after planting, respectively) in all locations analysed. In terms of beta-diversity of bacterial populations, both the location ($R^2$=0.24) and the phenological stage ($R^2$=0.21) have similar-major-effects, with the treatment ($R^2$=0.01) having a minor effect. However, for fungal populations, location dominates as the main driver of the beta-diversity patterns ($R^2$=0.36), with the phenological state having a much lower impact ($R^2$=0.08) than in bacterial populations, and, again, the treatment ($R^2$=0.01) showed a minor effect. The returned outputs also captured effects of different edaphological and weather conditions at each of these locations, which are major drivers of the soil microbial populations. The significant differences between microbial community compositions before and after planting can be clearly seen where, despite large differences between locations, T1 and T2 samples clustered in all the three locations, away from their respective T0, especially in the case of bacterial populations.

Regarding alpha-diversity the model returned outputs demonstrating features and corresponding pertubations related to planting in reducing the diversity of bacterial and fungal populations, as shown for both OTUs richness and Shannon (H') index values from T0 to T1. This trend was extended until time T2 in most cases—with the exception of the Shannon index for bacterial populations indicating that the phenological stage of the plant is the main driver of changes at the alpha-diversity level in both bacterial and fungal populations. Comparing control versus treated samples at the same time point, the models also returned significant changes at T1 for bacterial richness and Shannon index as well as fungal Shannon index for bacterial and fungal populations.

At the taxonomy level, despite clear population dynamic patterns from T0 to T2 sampling times in all the three locations and in both treated and untreated samples, samples from all three locations and times shared some of the most abundant genera for both bacterial and fungal communities. Among the top fungal genera shared across samples in our study (core fungal species) we found *Cryptococcus, Mortierella*, and *Alternaria*. Outputs of the model did not indicate a durable impact of the treatment on the soil and rhizosphere microbial communities in terms of major taxa, and alpha- and beta-diversity (, but a clear temporal-cyclical-dynamics which differentiates soil (T0 and T3) and rhizosphere (T1 and T2) samples.

2.5.2.2 Elements of Microbiome Composition and Structure can be Effectively Modulated by Use of a *B. subtilis*-Based Biostimulant To dissect the specific effect of the biostimulant over the microbial composition across time at each location, the model was configured to process fold change of each OTU in the treatment group from T0 to T1 (and from T0 to T2) vs. the fold change in the control group at the same time intervals per location. Out of 17,241 unique bacterial OTUs in the samples of the study, 16 changed significantly from T0 to T1 (, and 100 from T0 to T2. These OTUs belong to 73 genera, of which, 13 changed significantly in at least two locations: *Bacillus, Bradyrhizobium, Clostridium, Novosphingobium, Rhodoplanes, Sphingomonas, Sphingopyxis*, and *Woodsholea* in Grant and Sutton; *Agromyces,* *Flavobacterium, Pedobacter*, and *Sporosarcina* in Sutton and White Pigeon; and *Stenotrophomonas* in Grant and White Pigeon. For fungi, out of 1,702 unique OTUs, 10 OTUs changed significantly from T0 to T1, and 32 from T0 to T2. These OTUs belong to 30 genera, of which, one changed significantly in at least two locations: *Cryptococcus* in Sutton and White Pigeon. Thus, despite the location and phenological stage having a larger effect in the diversity of microorganism populations than treatment, the inoculant still generated common detectable abundance changes in at least two locations for several taxonomic groups, some of which have known functionally relevant roles (*Bacillus, Bradyrhizobium, Flavobacterium, Pedobacter, Sphingomonas*, and *Stenotrophomonas*).

In order to get a deeper understanding of how the structure of the bacterial and fungal communities, and therefore the ecological relationships among microorganisms, impacts the effect of the bacterial inoculant, the model was configured to analyze the co-inclusion and co-exclusion patterns between OTUs in each sample. By processing the network properties of local communities inferred from the co-inclusion and co-exclusion patterns of a reference metacommunity, the model generated ecological emergent properties (i.e. niche specialization, level of competition) of interest for the understanding of microbiome functionality. The model was configured to extract metacommunity level information based on all samples. As an initial filter, for bacteria, the model retained OTUs that were detected in at least 30% of the entire dataset, and 90% for fungal communities (e.g., due to the disproportionate number of unique OTUs detected in 16S vs. ITS sequencing). The model also filtered out OTU pairs that were not significantly ($p<0.05$) co-included or co-excluded. This resulted in metacommunity networks consisting of 3,339 nodes for bacteria (19.4% of the total 17,241 bacterial OTUs) and 447 nodes for fungi (26.3% of the total 1,702 fungal OTUs), which on average captured 92.11% of the bacterial abundance and 98.62% of the fungal abundance of the samples being processed. The model then processed outputs to determine the structure of local microbiome communities (e.g., based on just the nodes present in each individual sample), for detection of changes in network properties that are associated with the application of the biostimulant at a specific location over time.

As observed, there was a significant decrease in fungal co-inclusion transitivity and bacterial co-inclusion from T0 to T1 in the treated samples when compared to untreated ones. As such, model outputs can be used to characterize aspects and effects of any perturbation (e.g., human intervention) in a crop, which alters the structure of microbial communities of the soil, and a decreased transitivity on the fungal co-inclusion network is one of the best indicators of these alterations. Outputs of the models also depicted a lagged effect (at T2) of the treatment in modifying some network properties of the bacterial communities samples of locations being assessed. In one location, the bacterial co-inclusion proportion increases from T0 to T2 (in contrast to the decrease from T0 to T1), and at the same time the transitivity of the co-inclusion bacterial network increases. In another location, both the bacterial co-inclusion proportion as well as the bacterial co-exclusion proportion increase from T0 to T2. Thus, the model returned outputs indicating significant treatment-mediated effects over the fungal and bacterial community that decrease from T0 to T1, and then increase in T2.

2.5.2.3 Elements of Microbiome Composition and Structure Help Predict Potato Yield The model also included architecture for fitting a Random Forest model configured to predict if a soil sample comes from a block with yield characteristics (e.g., yield ≤30 t/Ha or >30 t/Ha), based on its microbiome composition and structure using multivariate compositional data (Principal Components from a beta-diversity ordination) and local network properties. Data from soil samples was split into a training dataset and a test dataset. The result of this model showed high predictive accuracy and highlights 4 variables (i.e., 2 network properties and 2 compositional) as the most important predictors of yield even with a higher importance than location. As such, features generated and processed, where features were associated with the structure of fungal communities (i.e. fungal co-inclusion transitivity and co-exclusion proportion), provided higher predictive value than the structure of bacterial communities, in assessing effects of products (e.g., biostimulants) and guiding management practices. The model returned an inverse correlation between the co-inclusion transitivity of rhizosphere fungal communities and the yield found in the potato cultivars. This is a particularly important observation for understanding the effect of the *B. subtilis* based biostimulant assayed here in shaping the structure of fungal communities as a potential mechanism of action when increasing the yield. In going from T0 to T1 the increase in fungal co-inclusion transitivity in one location was greater in the untreated samples than the treated ones, and this difference is significant. In another location—where a smaller but significant effect of the treatment increasing yield was also found—in going from T0 to T1 there was also a smaller increase in fungal co-inclusion network transitivity in the treated plots when compared to the untreated ones.

Two other compositional variables (e.g., PC3 and PC1) contributing to the predictive power of the model fitted were also explored by looking at the taxonomy of the OTUs in there showing a significant correlation with the yield.

With the assumption that yield is constant for all samples within a location, the model was configured to convert yield to a categorical variable (e.g., ≤30 t/Ha, >30 t/Ha). The distribution of the yield data was bimodal, and thus it seemed logical to divide the categories on a zero-probability density point for the bimodal distribution. However, in order to assess if this decision had an impact in the features identified as important by the yield predictive model presented here, the model also investigated splitting yield into more than two categories (e.g., ≤26 t/Ha, >26 t/Ha to ≤35 t/Ha, >35 t/Ha) or four (≤20 t/Ha, >20 t/Ha to 26 t/Ha; >26 t/Ha to ≤35 t/Ha, >35 t/Ha) categories. The model returned outputs that indicated that fungal co-inclusion transitivity and fungal co-exclusion proportion always had higher importance than location, independent of the number of yield categories used. In the model with three yield categories the bacterial co-exclusion proportion also had higher importance than location, whereas in the model with four yield categories, fungal co-inclusion modularity and PC12 had higher importance than location.

The ML yield model based on bacterial and fungal communities of soil and their structure, was thus able to predict with relatively high accuracy whether a potato plot will have a yield of more or less than a threshold level 30 t/Ha. Furthermore, with inclusion of product-associated perturbations (e.g., application of a bioinoculant), the yield model also was able to assess effects (e.g., with respect to structure of fungal communities, etc.) of product-associated perturbations. In particular, the model returned outputs that indicated that application of a bioinoculant resulted in a smaller increase of fungal co-inclusion transitivity of treated plots when compared to untreated plots. As such, application of the bioinoculant produces an effect in the soil microbial populations that resembles the effect of traditional management when compared to organic or biodynamic management. Furthermore, the effect of the soil bioinoculant tested here was transitory as demonstrated by the non significant alpha-diversity changes for fungal and bacterial communities between T0 and T3 in treated vs. untreated plots. Thus, *Bacillus subtilis* QST 713 seems to help the soil microbiota adopt a conformation with lower fungal co-inclusion network transitivity than expected from untreated plots which is conducive to improved yield, but in a sustainable manner (the fungal communities return to their original stage post harvest). Such insights can be used to guide application of products with transient or long term effects, and management practices according to executed actions described above.

In variations of these examples, the methods can be used to build an extensive database of crops/samples from different locations, where networks are built and characterized based upon metacommunities. These processes and generated databases can thus be used to obtain expected co-inclusion and/or co-exclusion connections when processing additional samples.

2.5.3 Example Insights and Interventions with Respect to Apple Peel Samples and Management Practices In another example, the model processed network features from samples of apple peels from multiple locations, where the associated apple trees were subject to varying management practices (e.g., conventional management practices, organic management practices). The model was able to assess various network properties (described above) in relation to standard deviations above mean values across the samples. The model was configured to return outputs indicating the effect of orchard type and managemenet practices (e.g., with fitting of a linear model to data). Various network properties, changes in network properties over time, and derivative emergent properties were used as inputs to predict management practices associated with the samples, with applications in organic and biodynamic certification, guiding interventions for improving productivity, increasing shelf-life, and/or sustainability of processes.

3. System

Figure 12:
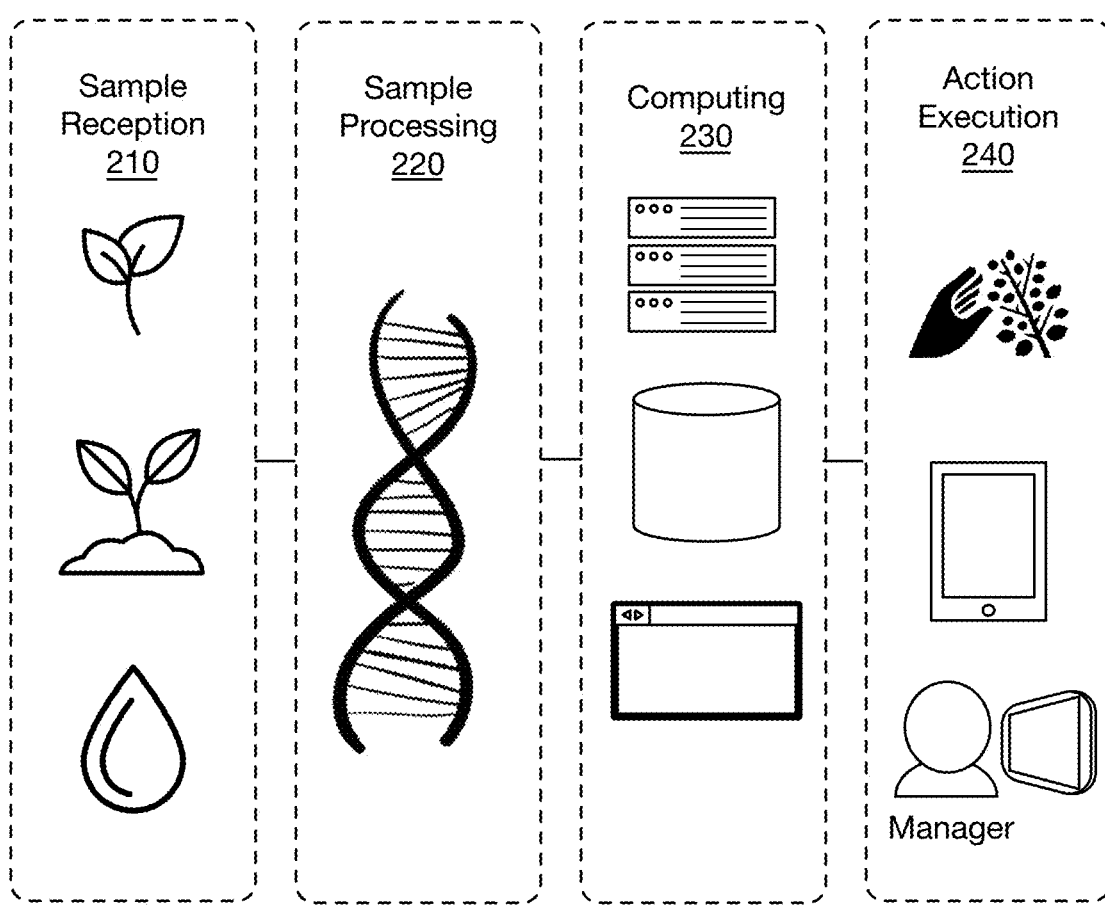
FIG. 12 depicts a schematic of an embodiment of a system for agriculture site analysis.

As shown in FIG. 12, a system 200 for characterization and improvement of an agricultural site includes: one or more sample reception subsystems 210; one or more sample processing subsystems 220 in communication with the sample reception subsystems 210; a computing platform 230 comprising one or more processing subsystems comprising non-transitory computer-readable medium comprising instructions stored thereon, that when executed by the processing subsystems perform one or more steps of methods described above; and one or more action execution subsystems 240 configured to execute actions informed by processes of the computing platform 230. In variations, the action execution subsystems 240 can be configured to execute control instructions generated by the computing platform 230, where control instructions can involve instructions for controlling operation modes of one or more of: watering subsystems (e.g., in relation to water distribution through conduits and/or sprinklers to the agriculture site(s)); product delivery subsystems in communication with watering subsystems (e.g., delivery subsystems in communication with watering subsystems through fluidic components, valves, etc.); robotic crop handling subsystems (e.g., in relation to removal of pathogen-affected crop portions); robotic crop picking subsystems (e.g., in relation to automated harvesting at optimal time periods in relation to improving production, in relation to efficiency of new production generation post-harvesting, in relation to minimization of wasted product, etc.); robotic nutrient delivery subsystems (e.g., in relation to initiating delivery, in relation to stopping delivery, in relation to adjusting frequency of delivery, in relation to adjusting delivery dosages, etc.); greenhouse subsystems; temperature control subsystems (e.g., in relation to modes for controlling environmental temperature of the agriculture site, etc.); light control subsystems (e.g., in relation to modes for controlling environmental light of the agriculture site, in relation to transitioning between on and off states, in relation to light spectrum delivered, etc.); gas environment subsystems (e.g., in relation to modes for controlling environmental gas composition of the agriculture site, etc.); humidity control subsystems (e.g., in relation to modes for controlling environmental humidity levels of the agriculture site, etc.); pressure control subsystems (e.g., in relation to modes for controlling environmental pressure of the agriculture site, etc.); and other suitable subsystem(s) of the agriculture site(s).

Embodiments of the system 200 are configured to perform one or more portions of methods described above; however, variations of the system 200 can be configured to perform other suitable methods.

4. Conclusions

The invention(s) describe decipher different ecological strategies that bacterial, fungal, and/or other organism communities adopt in face of different levels of farming intensification and product use, and explored on how these may impact soil health in terms of external factors and plant pathogens. In applications, outputs of the invention(s) can guide interventions and/or other practices to improve agriculture sites, as observed community assembly strategies. In examples, a collaborative well-mixed habitat in soils under biodynamic management with potentially higher resistance towards, at least, temperature variations, or a more divided habitat, with fungi belonging to more niches but with lower reaction range to temperature in soils under conventional management. Under this framework, the inventions have practical applications with relevance for agriculture sustainability, and with respect to interventions that can be designed to drive a better future for agro-ecosystems. For instance, evaluating how emergent properties change during time-series, may give clear indications about the resistance and resilience of fungal communities, or shed light into the dynamics of soils under different anthropogenic disturbances. For now, the defined ecological emergent properties may be used as biomarkers to measure the effect of farming practices or temperature change consequences in the health status of soils. Given the key role that microorganisms play in agri-food systems in general, and in the wine industry in particular, these findings are useful for establishing monitoring programs of crop-associated microbial diversity, supporting the work of alliances such as the soil health institute the U.S. department of agriculture, or the global initiative of crop microbiome and sustainable agriculture, while promoting soil healthiness through agriculture sustainable strategies.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the art will recognize from the previous detailed description and from the figures and claims, modifications and changes can be made to the preferred embodiments of the invention without departing from the scope of this invention defined in the following claims.

APPENDIX A

TABLE 1

| Network property | Spain | | | USA | | |
|---|---|---|---|---|---|---|
| | min | max | mean | min | max | mean |
| Co-occurrence proportion | 0.116 | 0.405 | 0.187 | 0.086 | 0.216 | 0.13 |
| Clustering (+) | 0.446 | 0.934 | 0.595 | 0.344 | 0.67 | 0.463 |
| Modularity (+) | 0.003 | 0.427 | 0.14 | 0.081 | 0.316 | 0.178 |
| Nr modules (+) | 2 | 21 | 4.846 | 2 | 12 | 3.817 |
| Ave. p. length (+) | 1.189 | 2.134 | 1.643 | 1.574 | 1.889 | 1.755 |
| Assortativity (+) | 0.078 | 0.735 | 0.237 | 0.072 | 0.47 | 0.216 |
| Co-exclusion proportion | 0 | 0.038 | 0.007 | 0.001 | 0.015 | 0.005 |
| Clustering (−) | 0 | 0.232 | 0.019 | 0 | 0.027 | 0.004 |
| Connected comp (−) | 1 | 6 | 1.914 | 1 | 9 | 1.977 |
| Modularity (−) | 0.002 | 0.616 | 0.231 | 0.065 | 0.84 | 0.383 |
| Nr modules (−) | 2 | 215 | 24.417 | 5 | 130 | 29.54 |
| Ave. p. length (−) | 2 | 3.891 | 2.935 | 1.231 | 4.116 | 3.379 |
| Assortativity (−) | −0.798 | −0.111 | −0.417 | −0.573 | −0.016 | −0.263 |

TABLE 2

| Variable | ANOVA p | Net. Property |
|---|---|---|
| Country | 0.0000 | Assortativity (−) |
| | 0.0000 | Ave. p. length (−) |
| | 0.0000 | Ave. p. length (+) |
| | 0.0001 | Co-exclusion proportion |
| | 0.0000 | Co-occurrence proportion |
| | 0.0011 | Nr modules (+) |
| | 0.0000 | Modularity (−) |
| | 0.0000 | Modularity (+) |
| | 0.0000 | Clustering coeff (−) |
| | 0.0000 | Clustering coeff (+) |
| interaction CxM | 0.0048 | Assortativity (−) |
| | 0.0076 | Ave. p. length (−) |
| | 0.0000 | Ave. p. length (+) |
| | 0.0000 | Co-occurrence proportion |

TABLE 2-continued

| Variable | ANOVA p | Net. Property |
|---|---|---|
| | 0.0049 | Nr modules (−) |
| | 0.0044 | Nr modules (+) |
| | 0.0035 | Modularity (+) |
| | 0.0001 | Clustering coeff (+) |
| Management | 0.0001 | Assortativity (−) |
| type | 0.0001 | Assortativity (+) |
| | 0.0000 | Ave. p. length (+) |
| | 0.0039 | Connected components (−) |
| | 0.0000 | Co-exclusion proportion |
| | 0.0000 | Co-occurrence proportion |
| | 0.0000 | Modularity (+) |
| | 0.0165 | Clustering coeff (−) |
| | 0.0000 | Clustering coeff (+) |

TABLE 3

| Disease | Pathogen sp. | presence |
|---|---|---|
| *Armillaria* root rot | *Armillaria mellea* | present |
| *Aspergillus* rot | *Aspergillus carbonarius* | present |
| Black foot disease | *Ilyonectria robusta* | present |
| Black foot disease | *Campylocarpon fasciculare* | present |
| Black foot disease | *Ilyonectria liriodendri* | present |
| Black foot disease | *Dactylonectria estremocensis* | present |
| Black foot disease | *Campylocarpon pseudofasciculare* | not present |
| *Botryosphaeria* dieback | *Botryoshaeria dothidea* | present |
| *Botryosphaeria* dieback | *Lasiodiplodia missouriana* | present |
| *Botryosphaeria* dieback | *Neofusicoccum parvum* | present |
| *Botryosphaeria* dieback | *Neofusicoccum australe* | not present |
| *Botrytis* bunch rot | *Botrytis cinerea* | not present |
| Esca Complex | *Phaeomoniella chlamydospora* | present |
| Esca Complex | *Phaeoacremonium minimum* | present |
| Esca Complex | *Phaeoacremonium hipanicum* | present |
| Esca Complex | *Fomitiporia aethiopica* | not present |
| Esca Complex | *Phaeoacremonium inflatipes* | not present |
| Esca Complex | *Stereum hirsutum* | not present |
| *Eutypa* dieback | *Eutypella citricola* | present |
| *Eutypa* dieback | *Cryptovalsa ampelina* | present |
| *Eutypa* dieback | *Diatrype stigma* | present |
| *Eutypa* dieback | *Eutypa lata* | not present |
| Petri disease | *Cadophora luteo-olivacea* | present |
| Phomopsis dieback | *Diaporthe ampelina* | present |
| *Verticillium* wilt | *Verticillium dahliae* | present |

TABLE 4

| sample | country | management |
|---|---|---|
| Es1 | spain | nomanagement |
| Es2 | spain | nomanagement |
| Es3 | spain | nomanagement |
| Es4 | spain | nomanagement |
| Es5 | spain | nomanagement |
| Es6 | spain | nomanagement |
| Es7 | spain | management_yes |
| Es8 | spain | management_yes |
| Es9 | spain | management_yes |
| Es10 | spain | management_yes |
| Es11 | spain | management_yes |
| Es12 | spain | management_yes |
| Es13 | spain | management_yes |
| Es14 | spain | management_yes |
| Es15 | spain | management_yes |
| Es16 | spain | management_yes |
| Es17 | spain | management_yes |
| Es18 | spain | management_yes |
| Es19 | spain | management_yes |
| Es20 | spain | management_yes |
| Es21 | spain | management_yes |
| Es22 | spain | management_yes |
| Es23 | spain | management_yes |
| Es24 | spain | management_yes |
| Es25 | spain | management_yes |
| Es26 | spain | management_yes |
| Es27 | spain | management_yes |
| Es28 | spain | management_yes |
| Es29 | spain | management_yes |
| Es30 | spain | management_yes |
| Es31 | spain | management_yes |
| Es32 | spain | management_yes |
| Es33 | spain | management_yes |
| Es34 | spain | management_yes |
| Es35 | spain | management_yes |
| Es36 | spain | management_yes |
| Es37 | spain | management_yes |
| Es38 | spain | management_yes |
| Es39 | spain | management_yes |
| Es40 | spain | management_yes |
| Es41 | spain | management_yes |
| Es42 | spain | management_yes |
| Es43 | spain | management_yes |
| Es44 | spain | management_yes |
| Es45 | spain | management_yes |
| Es46 | spain | management_yes |
| Es47 | spain | management_yes |
| Es48 | spain | management_yes |
| Es49 | spain | management_yes |
| Es50 | spain | management_yes |
| Es51 | spain | management_yes |
| Es52 | spain | management_yes |
| Es53 | spain | management_yes |
| Es54 | spain | management_yes |
| Es55 | spain | management_yes |
| Es56 | spain | management_yes |
| Es57 | spain | management_yes |
| Es58 | spain | management_yes |
| Es59 | spain | management_yes |
| Es60 | spain | management_yes |
| Es61 | spain | management_yes |
| Es62 | spain | management_yes |
| Es63 | spain | management_yes |
| Es64 | spain | management_yes |
| Es65 | spain | management_yes |
| Es66 | spain | management_yes |
| Es67 | spain | management_yes |
| Es68 | spain | management_yes |
| Es69 | spain | management_yes |
| Es70 | spain | management_yes |
| Es71 | spain | management_yes |
| Es72 | spain | management_yes |
| Es73 | spain | management_yes |
| Es74 | spain | management_yes |
| Es75 | spain | management_yes |
| Es76 | spain | management_yes |
| Es77 | spain | management_yes |
| Es78 | spain | management_yes |
| Es79 | spain | management_yes |
| Es80 | spain | management_yes |
| Es81 | spain | management_yes |
| Es82 | spain | management_yes |
| Es83 | spain | management_yes |
| Es84 | spain | management_yes |
| Es85 | spain | management_yes |
| Es86 | spain | management_yes |
| Es87 | spain | management_yes |
| Es88 | spain | management_yes |
| Es89 | spain | management_yes |
| Es90 | spain | management_yes |
| Es91 | spain | management_yes |
| Es92 | spain | management_yes |
| Es93 | spain | management_yes |
| Es94 | spain | management_yes |
| Es95 | spain | management_yes |
| Es96 | spain | management_yes |
| Es97 | spain | management_yes |
| Es98 | spain | management_yes |
| Es99 | spain | management_yes |
| Es100 | spain | management_yes |
| Es101 | spain | management_yes |
| Es102 | spain | management_yes |

TABLE 4-continued

| sample | country | management |
|---|---|---|
| Es103 | spain | management_yes |
| Es104 | spain | management_yes |
| Es105 | spain | management_yes |
| Es106 | spain | management_yes |
| Es107 | spain | management_yes |
| Es108 | spain | management_yes |
| Es109 | spain | management_yes |
| Es110 | spain | management_yes |
| Es111 | spain | management_yes |
| Es112 | spain | management_yes |
| Es113 | spain | management_yes |
| Es114 | spain | management_yes |
| Es115 | spain | management_yes |
| Es116 | spain | management_yes |
| Es117 | spain | management_yes |
| Es118 | spain | management_yes |
| Es119 | spain | management_yes |
| Es120 | spain | management_yes |
| Es121 | spain | management_yes |
| Es122 | spain | management_yes |
| Es123 | spain | management_yes |
| Es124 | spain | management_yes |
| Es125 | spain | management_yes |
| Es126 | spain | management_yes |
| Es127 | spain | management_yes |
| Es128 | spain | management_yes |
| Es129 | spain | management_yes |
| Es130 | spain | management_yes |
| Es131 | spain | management_yes |
| Es132 | spain | management_yes |
| Es133 | spain | management_yes |
| Es134 | spain | management_yes |
| Es135 | spain | management_yes |
| Es136 | spain | management_yes |
| Es137 | spain | management_yes |
| Es138 | spain | management_yes |
| Es139 | spain | management_yes |
| Es140 | spain | management_yes |
| Es141 | spain | management_yes |
| Es142 | spain | management_yes |
| Es143 | spain | management_yes |
| Es144 | spain | management_yes |
| Es145 | spain | management_yes |
| Es146 | spain | management_yes |
| Es147 | spain | management_yes |
| Es148 | spain | management_yes |
| Es149 | spain | management_yes |
| Es150 | spain | management_yes |
| Es151 | spain | management_yes |
| Es152 | spain | management_yes |
| Es153 | spain | management_yes |
| Es154 | spain | management_yes |
| Es155 | spain | management_yes |
| Es156 | spain | management_yes |
| Es157 | spain | management_yes |
| Es158 | spain | management_yes |
| Es159 | spain | management_yes |
| Es160 | spain | management_yes |
| Es161 | spain | management_yes |
| Es162 | spain | management_yes |
| Es163 | spain | management_yes |
| Es164 | spain | management_yes |
| Es165 | spain | management_yes |
| Es166 | spain | management_yes |
| Es167 | spain | management_yes |
| Es168 | spain | management_yes |
| Es169 | spain | management_yes |
| Es170 | spain | management_yes |
| Es171 | spain | management_yes |
| Es172 | spain | management_yes |
| Es173 | spain | management_yes |
| Es174 | spain | management_yes |
| Es175 | spain | management_yes |
| Us1 | usa | management_yes |
| Us2 | usa | management_yes |
| Us3 | usa | management_yes |
| Us4 | usa | management_yes |
| Us5 | usa | management_yes |
| Us6 | usa | management_yes |
| Us7 | usa | management_yes |
| Us8 | usa | management_yes |
| Us9 | usa | management_yes |
| Us10 | usa | management_yes |
| Us11 | usa | management_yes |
| Us12 | usa | management_yes |
| Us13 | usa | management_yes |
| Us14 | usa | management_yes |
| Us15 | usa | management_yes |
| Us16 | usa | management_yes |
| Us17 | usa | management_yes |
| Us18 | usa | management_yes |
| Us19 | usa | management_yes |
| Us20 | usa | management_yes |
| Us21 | usa | management_yes |
| Us22 | usa | management_yes |
| Us23 | usa | management_yes |
| Us24 | usa | management_yes |
| Us25 | usa | management_yes |
| Us26 | usa | management_yes |
| Us27 | usa | management_yes |
| Us28 | usa | management_yes |
| Us29 | usa | management_yes |
| Us30 | usa | management_yes |
| Us31 | usa | management_yes |
| Us32 | usa | management_yes |
| Us33 | usa | management_yes |
| Us34 | usa | management_yes |
| Us35 | usa | management_yes |
| Us36 | usa | management_yes |
| Us37 | usa | management_yes |
| Us38 | usa | management_yes |
| Us39 | usa | management_yes |
| Us40 | usa | nomanagement |
| Us41 | usa | nomanagement |
| Us42 | usa | nomanagement |
| Us43 | usa | nomanagement |
| Us44 | usa | nomanagement |
| Us45 | usa | nomanagement |
| Us46 | usa | nomanagement |
| Us47 | usa | nomanagement |
| Us48 | usa | nomanagement |
| Us49 | usa | management_yes |
| Us50 | usa | management_yes |
| Us51 | usa | management_yes |
| Us52 | usa | management_yes |
| Us53 | usa | management_yes |
| Us54 | usa | management_yes |
| Us55 | usa | management_yes |
| Us56 | usa | management_yes |
| Us57 | usa | management_yes |
| Us58 | usa | management_yes |
| Us59 | usa | management_yes |
| Us60 | usa | management_yes |
| Us61 | usa | management_yes |
| Us62 | usa | management_yes |
| Us63 | usa | management_yes |
| Us64 | usa | management_yes |
| Us65 | usa | management_yes |
| Us66 | usa | management_yes |
| Us67 | usa | nomanagement |
| Us68 | usa | management_yes |
| Us69 | usa | nomanagement |
| Us70 | usa | management_yes |
| Us71 | usa | management_yes |
| Us72 | usa | management_yes |
| Us73 | usa | management_yes |
| Us74 | usa | management_yes |
| Us75 | usa | management_yes |
| Us76 | usa | management_yes |
| Us77 | usa | management_yes |
| Us78 | usa | management_yes |
| Us79 | usa | management_yes |
| Us80 | usa | management_yes |
| Us81 | usa | management_yes |
| Us82 | usa | management_yes |
| Us83 | usa | management_yes |

TABLE 4-continued

| sample | country | management |
|---|---|---|
| Us84 | usa | management_yes |
| Us85 | usa | management_yes |
| Us86 | usa | management_yes |
| Us87 | usa | management_yes |
| Us88 | usa | management_yes |
| Us89 | usa | management_yes |
| Us90 | usa | management_yes |
| Us91 | usa | management_yes |
| Us92 | usa | management_yes |
| Us93 | usa | management_yes |
| Us94 | usa | management_yes |
| Us95 | usa | management_yes |
| Us96 | usa | management_yes |
| Us97 | usa | management_yes |
| Us98 | usa | management_yes |
| Us99 | usa | management_yes |
| Us100 | usa | management_yes |
| Us101 | usa | management_yes |
| Us102 | usa | management_yes |
| Us103 | usa | nomanagement |
| Us104 | usa | nomanagement |
| Us105 | usa | nomanagement |
| Us106 | usa | nomanagement |
| Us107 | usa | nomanagement |
| Us108 | usa | nomanagement |
| Us109 | usa | nomanagement |
| Us110 | usa | nomanagement |
| Us111 | usa | nomanagement |
| Us112 | usa | nomanagement |
| Us113 | usa | nomanagement |
| Us114 | usa | nomanagement |
| Us115 | usa | nomanagement |
| Us116 | usa | nomanagement |
| Us117 | usa | nomanagement |
| Us118 | usa | nomanagement |
| Us119 | usa | nomanagement |
| Us120 | usa | nomanagement |
| Us121 | usa | nomanagement |
| Us122 | usa | nomanagement |
| Us123 | usa | nomanagement |
| Us124 | usa | nomanagement |
| Us125 | usa | nomanagement |
| Us126 | usa | nomanagement |
| Us127 | usa | nomanagement |
| Us128 | usa | nomanagement |
| Us129 | usa | nomanagement |
| Us130 | usa | management_yes |
| Us131 | usa | nomanagement |
| Us132 | usa | management_yes |
| Us133 | usa | management_yes |
| Us134 | usa | management_yes |
| Us135 | usa | management_yes |
| Us136 | usa | management_yes |
| Us137 | usa | management_yes |
| Us138 | usa | management_yes |
| Us139 | usa | management_yes |
| Us140 | usa | management_yes |
| Us141 | usa | management_yes |
| Us142 | usa | management_yes |
| Us143 | usa | management_yes |
| Us144 | usa | management_yes |
| Us145 | usa | management_yes |
| Us146 | usa | management_yes |
| Us147 | usa | nomanagement |
| Us148 | usa | management_yes |
| Us149 | usa | management_yes |
| Us150 | usa | management_yes |
| Us151 | usa | management_yes |
| Us152 | usa | management_yes |
| Us153 | usa | management_yes |
| Us154 | usa | nomanagement |
| Us155 | usa | management_yes |
| Us156 | usa | nomanagement |
| Us157 | usa | nomanagement |
| Us158 | usa | management_yes |
| Us159 | usa | management_yes |
| Us160 | usa | management_yes |
| Us161 | usa | management_yes |
| Us162 | usa | nomanagement |
| Us163 | usa | nomanagement |
| Us164 | usa | nomanagement |
| Us165 | usa | nomanagement |
| Us166 | usa | nomanagement |
| Us167 | usa | management_yes |
| Us168 | usa | management_yes |
| Us169 | usa | management_yes |
| Us170 | usa | nomanagement |
| Us171 | usa | management_yes |
| Us172 | usa | management_yes |
| Us173 | usa | nomanagement |
| Us174 | usa | nomanagement |
| Us175 | usa | management_yes |

What is claimed is:

1. A method for characterization and improvement of an agricultural site, the method comprising:
   receiving a set of agriculture samples from an agriculture site, in association with a perturbation to the agriculture site;
   generating a sample dataset upon processing the set of agriculture samples with a set of sample processing operations that characterize microbial composition of said set of agriculture samples, wherein the set of sample processing operations comprises processing Bayes factors associated with connections between at least one of multiple operational taxonomic units (OTUs) and multiple amplicon sequence variants (ASVs) represented in sequenced nucleic acids from the set of agriculture samples, for use as edge-weights for weighted directed networks;
   generating a set of features upon performing a set of transformation operations upon the sample dataset, wherein the set of features is associated with a set of network properties of organisms of the set of agriculture samples;
   returning an analysis characterizing a status of the agriculture site in relation to the perturbation, upon processing the set of features; and
   executing an action for at least one of maintaining and improving the status of the agriculture site, based upon the analysis.

2. The method of claim 1, wherein the set of agriculture samples comprise at least one of: a soil sample, a substrate sample, a root sample, a foliage sample, a liquid sample, and a crop-derived sample.

3. The method of claim 1, wherein the perturbation comprises a management practice comprising one of: a conventional management practice, an organic management practice, and a biodynamic management practice.

4. The method of claim 1, wherein the perturbation comprises a regenerative practice comprising application of one or more of: a cover crop, silvopasture, managed grazing, and intercropping.

5. The method of claim 1, wherein the perturbation comprises a biological input comprising one or more of: a biostimulant, a biofertilizer, a biocontrol agent, a biopesticide, compost, and a biodynamic preparation, wherein the biological input is applied by one or more of: a broadcast spray, an in-furrow spray, seed treatment, and application to soil.

6. The method of claim 1, wherein the analysis returns predictions of one or more of: resilience to disease risk, terroir, soil health, nutrient metabolism, yield, tissue nutrient composition, and shelf-life associated with the agriculture site.

7. The method of claim 1, wherein the perturbation comprises a natural ecological disturbance.

8. The method of claim 1, wherein receiving the set of agriculture samples comprises transitioning a robotic apparatus into a sample reception mode in which the robotic apparatus traverses the agriculture site in coordination with retrieval of the set of agriculture samples.

9. The method of claim 1, wherein the set of agriculture samples is received from a set of locations within a metacommunity.

10. The method of claim 1, wherein the set of sample processing operations comprises sequencing of a set of target regions of nucleic acid material from the set of agriculture samples, wherein the set of target regions comprises a phylogenetic marker comprising at least one of: a 16s region, and an ITS region.

11. The method of claim 10, wherein the set of sample processing operations further comprises one or more of: clustering non-singleton sequences of the set of target regions into a set of operational taxonomic units (OTUs) and clustering sequences with a difference of one nucleotide into a set of amplicon sequence variants (ASVs).

12. The method of claim 11, wherein generating the set of features upon performing the set of transformation operations comprises: generating a community dataset, and at least one of: filtering OTUs of the set of OTUs and filtering ASVs of the set of ASVs based upon a threshold condition.

13. The method of claim 1, wherein the set of features comprises: a number of connected components, a modularity factor, a clustering coefficient, an average path length between network components, and an assortativity factor.

14. The method of claim 1 wherein the set of features characterize fungal community network arrangements represented at the agriculture site.

15. The method of claim 1, wherein the set of features characterize at least one of microbiome community composition and functional profile represented at the agriculture site.

16. The method of claim 15, wherein the set of features are derived from one or more of: bacteria, archaea, eukarya, and viruses.

17. The method of claim 1, wherein the set of sample processing operations comprises one or more of: generating a full metagenomic dataset, generating a metatranscriptomics dataset, and generating a proteomics dataset.

18. The method of claim 1, wherein the set of network properties comprise local network features extracted from a metacommunity network.

19. The method of claim 1, wherein returning the analysis comprises:
    training a model configured to process input features and return predicted characterizations of the agriculture site, wherein training the model comprises:
    collecting a training dataset derived from training samples, the training dataset corresponding to training samples subject to the perturbation to the agriculture site as well as control samples;
    applying one or more of the set of transformation operations to the training dataset; and
    training the model with the training dataset, the model comprising architecture for returning the analysis with identification of the effects of perturbation for test datasets, in one or more stages.

20. The method of claim 1, wherein executing the action comprises generating a notification indicating the status of the agriculture site and guidance for adjusting management of the agriculture site, and transmitting the notification to a manager of the agriculture site.

21. The method of claim 1, wherein executing the action comprises generating control instructions for one or more subsystems configured to execute operation modes associated with the perturbation, comprising a management practice.

22. The method of claim 21, wherein the one or more subsystems comprises a watering subsystem and a product delivery subsystem in communication with the agriculture site.

* * * * *

UNITED STATES PATENT AND TRADEMARK OFFICE
CERTIFICATE OF CORRECTION

Page 1 of 1

PATENT NO. : 11,933,775 B2
APPLICATION NO. : 17/119972
DATED : March 19, 2024
INVENTOR(S) : Alberto Acedo et al.

It is certified that error appears in the above-identified patent and that said Letters Patent is hereby corrected as shown below:

On the Title Page

At (72) Inventors:
After "Adrian Ferrero, La Bañeza (ES)"
Insert:
--;
Beatriz Garcia-Jimenez, Madrid (ES);
Sam Röttjers, Eygelshoven (NL)--

Signed and Sealed this
First Day of April, 2025

Coke Morgan Stewart
*Acting Director of the United States Patent and Trademark Office*